(12) United States Patent
Schoenafinger et al.

(10) Patent No.: US 7,838,528 B2
(45) Date of Patent: Nov. 23, 2010

(54) SUBSTITUTED BICYCLIC 8-PYRROLIDINOXANTHINES, METHODS FOR THEIR PRODUCTION, PHARMACEUTICAL FORMULATIONS AND THEIR USE

(75) Inventors: Karl Schoenafinger, Alzenau (DE); Gerhard Jaehne, Frankfurt (DE); Elisabeth Defossa, Idstein (DE); Lothar Schwink, Stadtallendorf (DE); Holger Wagner, Biberach/Mettenberg (DE); Christian Buning, Bonn (DE); Georg Tschank, Essenheim (DE); Ulrich Werner, Miehlen (DE)

(73) Assignee: sanofi-aventis Deutschland GmbH, Frankfurt am Main (DE)

( * ) Notice: Subject to any disclaimer, the term of this patent is extended or adjusted under 35 U.S.C. 154(b) by 723 days.

(21) Appl. No.: 11/623,770

(22) Filed: Jan. 17, 2007

(65) Prior Publication Data

US 2007/0167468 A1    Jul. 19, 2007

Related U.S. Application Data

(63) Continuation of application No. PCT/EP2005/008005, filed on Jul. 22, 2005.

(30) Foreign Application Priority Data

Aug. 6, 2004    (DE) .................. 10 2004 038 270

(51) Int. Cl.
  C07D 473/06    (2006.01)
  C07D 473/04    (2006.01)
  A61K 31/522    (2006.01)
  A61P 3/10    (2006.01)
  C07D 487/04    (2006.01)
  A61P 3/06    (2006.01)
(52) U.S. Cl. .................... 514/263.2; 544/268; 548/453
(58) Field of Classification Search ........................ None
  See application file for complete search history.

(56) References Cited

U.S. PATENT DOCUMENTS 3,472,861 A * 10/1969 Schulz et al. ................ 546/91
7,074,798 B2 * 7/2006 Yoshikawa et al. ........ 514/263.2
7,235,538 B2 * 6/2007 Kanstrup et al. ............... 514/81
7,495,004 B2 * 2/2009 Boggs et al. ........... 514/263.21
2004/0087587 A1 * 5/2004 Himmelsbach et al. .. 514/234.5
2007/0197563 A1 * 8/2007 Schoenafinger et al. .. 514/263.2

FOREIGN PATENT DOCUMENTS

| EP | 1338595 | 10/2003 |
| WO | 00063208 | 10/2000 |
| WO | 02/068420 | 9/2002 |

OTHER PUBLICATIONS

Biandine Laferrere et al., Effects of bombesin, of new bombesin agonist (BIM187) and a new antagonist (BIM189) on food intake in rats, in relation to cholecystokinin, European Journal of Pharmacology, 1992, vol. 215, pp. 23-28.
Corri Black et al., Meglitinide analogues for type 2 diabetes meilitus , The Cochrane Review, (2007).
Renzo Cescato et al., Bombesin Receptor Antagonists May Be Preferable to Agonists for Tumor Targeting, The Journal of Nuclear Medicine, 2008, vol. 49, No.2, pp. 318-326.

* cited by examiner

Primary Examiner—Mark L Berch
(74) Attorney, Agent, or Firm—Serena Farquharson-Torres

(57) ABSTRACT

Compounds for the treatment of elevated blood glucose levels and the physiological and metabolic disorders arising therefrom are disclosed and comprise novel substituted bicyclic 8-pyrrolidinoxanthines and their derivatives of formula I:

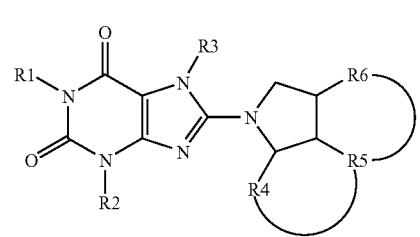

wherein the various R groups are hereinafter defined. The present invention also comprises pharmaceutical compositions comprising them as well as processes for the preparation of these compounds. Particular blood glucose disorders treatable thereby include type-2 diabetes, insulin resistance, hyperglycemia, arteriosclerotic diseases and the like.

7 Claims, No Drawings

SUBSTITUTED BICYCLIC 8-PYRROLIDINOXANTHINES, METHODS FOR THEIR PRODUCTION, PHARMACEUTICAL FORMULATIONS AND THEIR USE

CROSS-REFERENCE TO RELATED APPLICATIONS

This application is a continuation of International Patent Application No. PCT/EP2005/008005 filed on Jul. 22, 2005 which is incorporated herein by reference in it's' entirety which also claims the benefit of priority of German Patent Application No. 10/2004 038 270.0 filed on Aug. 6, 2004.

FIELD OF THE INVENTION

The present invention relates generally to compounds for the treatment of metabolic disorders such as type-2 diabetes, hyperglycemia, atherosclerotic diseases and the like. Specifically, the present invention relates to compounds that inhibit the activity of dipeptidyl peptidase IV (DPP-IV) and are thus very suitable for lowering the blood glucose level. More specifically, the present invention relates to substituted bicyclic 8-pyrrolidinalkylthioxanthines, their physiologically tolerated salts and functional derivatives and their therapeutic use as blood sugar-lowering agents among others.

BACKGROUND OF THE INVENTION

The enzyme dipeptidyl peptidase-IV (DPP-IV) inactivates a variety of bioactive peptides, including glucagon-like peptide-1 (GLP-1) and growth hormone releasing hormone (GHRH). Inhibiting DPP-IV in order to increase circulating GLP-1 is of interest as a treatment for Type II diabetes. Inactivation of DPP-IV may also increase circulating GHRH, potentially enhancing growth in domestic animals One such substituted bicyclic 8-pyrrolidinalkylthioxanthine, 8-(2-aminoethylsulfanyl)-1,3,7-trimethyl-3,7-dihydropurine-2,6-dione has been described in the literature. This Compound has been shown to act on the central nervous system (J. Med. Chem. (1966), 9 500-6). Inhibition of DPP-IV increases the circulating half-life of the incretin hormones GLP-1 and GIP, improving glucose tolerance in Type II diabetics. Complete inhibition of DPP-IV does not appear to be necessary as 2- to 3-fold increases in plasma concentrations of GLP-1 have been achieved in mice with inactivation of 84% to 96% of plasma DPP-IV. Thus, there has been much interest in developing DPP-IV inhibitors for the treatment of Type II diabetes and other metabolic disorders.

DPP-IV exists as both a membrane-spanning form present in cells throughout the body and a soluble circulating form. Both forms of DPP-IV have identical enzymatic activity and cleave a wide range of bioactive peptides in vitro, including hormones, neuropeptides, and chemokines. One potential regulatory role of DPP-IV is the inactivation of GHRH through cleavage of the active form, GHRH(1-44)-$NH_2$, to the N-terminally shortened inactive form, GHRH(3-44)-$NH_2$, While trypsin-like degradation of GHRH also occurs, in vitro studies using GHRH analogs designed to resist cleavage at the N-terminus have demonstrated that the primary degradation of GHRH is via DPP-IV. Substitution of Ala2 with Dali prevents DPP-IV proteolysis and administration of this analog increases GH release in swine up to 2-fold. The His1, Val2 analog of GHRH is also not degraded by DPP-IV in vitro, and it demonstrates increased plasma stability over native GHRH. GHRH analogs containing the His1, Val2 substitutions were 5.4- to 12.5-fold more potent than native GHRH in release of GH in swine. Thus, inhibition of DPP-IV in vivo may increase endogenous concentrations of GHRH and enhance GH secretion.

Compounds of similar structure have been described in the prior art such as the bicyclic xanthine derivatives and their use as DDPIV inhibitors described in U.S. Pat. No. 7,074,798 to Yoshikawa et. al. which is hereby incorporated by reference

SUMMARY OF THE INVENTION

The present invention involves substituted bicyclic 8-pyrrolidinoxanthines and their derivatives of formula I

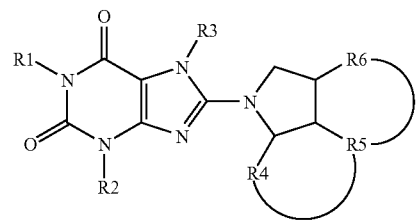

I wherein the various R groups are hereinafter defined. The present invention also comprises pharmaceutical compositions comprising them as well as processes for the preparation of these compounds and methods for the treatment of metabolic disorders through their administration such as type-2 diabetes, insulin resistance, hyperglycemia, arteriosclerotic diseases and the like.

DETAILED DESCRIPTION OF THE INVENTION

The substituted bicyclic 8-pyrrolidinoxanthines and their derivatives of formula I as set forth below

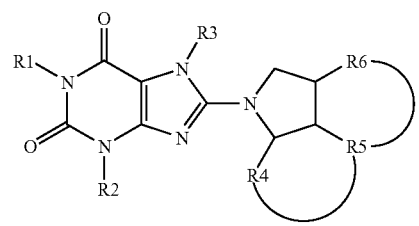

I

Are more specifically defined as follows:
R1, R2 and R3 which independently of one another are selected from the group consisting of H, $(C_1-C_{10})$-alkyl, $(C_3-C_{10})$-cycloalkyl, $(C_2-C_{10})$-alkenyl, $(C_2-C_{10})$-alkynyl, $(C_6-C_{10})$-aryl, heterocycle, where the alkyl, cycloalkyl, alkenyl, alkynyl, aryl and heterocyclic radicals may be substituted one or more times by F, Cl, Br, I, CN, $NO_2$, SH, OH, $(C_1-C_6)$-alkyl, —$CF_3$, —O—$CF_3$, —$SCF_3$, $(C_2-C_6)$-alkenyl, $(C_2-C_6)$-alkynyl, OR7, OP(O)(OR7)$_2$, NR7R8, NR7CONR7R8, COR7, OCOR7, OCOOR7, COOR7, CONR7R8, OCONR7R8, $(C_1-C_6)$-alkylene-OR7, $(C_1-C_6)$-alkylene-NR7R8, $(C_1-C_6)$-alkylene-NR7$SO_2$R7, $(C_1-C_6)$-alkylene-SR7, alkylene-S(O)R7, alkylene-S(O)$_2$R7, alkylene-S(O)$_2$NR7R8, $(C_1-C_6)$-alkylene-COR7, $(C_1-C_6)$-alkylene-COOR7, $(C_1-C_6)$-alkylene-CONR7R8, SR7, SOR7, $SO_2$R7, $SO_2$NR7R8, NR7$SO_2$R7, $(C_1-C_6)$- alkylene-$(C_3$-$C_{10})$-cycloalkyl, $(C_1$-$C_6)$-alkylene-$(C_6$-$C_{10})$-aryl, $(C_1$-$C_6)$-alkylene-heterocycle, $(C_3$-$C_{10})$-cycloalkyl, $(C_6$-$C_{10})$-aryl or heterocycle;

R7 and R8 which independently of one another are selected from the group consisting of H, $(C_1$-$C_6)$-alkyl, —$CF_3$, $(C_3$-$C_{10})$-cycloalkyl, $(C_6$-$C_{10})$-aryl, heterocyclyl, $(C_1$-$C_6)$-alkylene-CONR9R10, CONR9R10, $(C_1$-$C_6)$-alkylene-COOR9, COOR9, COR9, $(C_1$-$C_6)$-alkylene-COR9, $(C_1$-$C_6)$-alkylene-OR9, $(C_1$-$C_6)$-alkylene-NR9R10, $(C_1$-$C_6)$-alkylene-SR9, $(C_1$-$C_6)$-alkylene-S(O)R9, $(C_1$-$C_6)$-alkylene-S(O)$_2$R9, S(O)R9, S(O)$_2$R9, $(C_1$-$C_4)$-alkylene-$(C_6$-$C_{10})$-aryl or $(C_1$-$C_4)$-alkylene-heterocyclyl;

R9 and R10 which independently of one another are selected from the group consisting of H, $(C_1$-$C_6)$-alkyl, $(C_1$-$C_6)$-alkylene-$(C_6$-$C_{10})$-aryl, —$(C_6$-$C_{10})$-aryl, heterocyclyl, $(C_1$-$C_6)$-alkylene-heterocycle;

R4 and R5 which together form the group —$CH_2$—$CH_2$—NH—, wherein R6 is H,

R5 and R6 which together form the group —$CH_2$—NH—$CH_2$—, wherein R4 is H;

or the physiologically tolerated salt thereof.

Preferably, the present invention comprises compounds of the formula I in which one or more R-groups are selected from the group consisting of:

R1, R2 and R3 which independently of one another are selected from the group consisting of H, $(C_1$-$C_{10})$-alkyl, $(C_3$-$C_{10})$-cyclically, $(C_2$-$C_{10})$-alkenyl, $(C_2$-$C_{10})$-alkynyl, $(C_6$-$C_{10})$-aryl, heterocyclyl, where the alkyl, cycloalkyl, alkenyl, alkynyl, aryl and heterocyclyl radicals may be substituted one or more times by F, Cl, Br, I, CN, $NO_2$, SH, OH, $(C_1$-$C_6)$-alkyl, —$CF_3$, —$OCF_3$, —$SCF_3$, $(C_2$-$C_6)$-alkenyl, $(C_2$-$C_6)$-alkynyl, OR7, OP(O)(OR7)$_2$, NR7R8, NR7CONR7R8, COR7, OCOR7, OCOOR7, COOR7, CONR7R8, OCONR7R8, $(C_1$-$C_6)$-alkylene-OR7, $(C_1$-$C_6)$-alkylene-NR7R8, $(C_1$-$C_6)$-alkylene-NR7SO$_2$R7, $(C_1$-$C_6)$-alkylene-SR7, alkylene-S(O)R7, alkylene-S(O)$_2$R7, alkylene-S(O)$_2$NR7R8, $(C_1$-$C_6)$-alkylene-COR7, $(C_1$-$C_6)$-alkylene-COOR7, $(C_1$-$C_6)$-alkylene-CONR7R8, SR7, SOR7, SO$_2$R7, SO$_2$NR7R8, NR7SO$_2$R7, $(C_1$-$C_6)$-alkylene-$(C_3$-$C_{10})$-cycloalkyl, $(C_1$-$C_6)$-alkylene-$(C_6$-$C_{10})$-aryl, $(C_1$-$C_6)$-alkylene-heterocycle, $(C_3$-$C_{10})$-cycloalkyl, $(C_6$-$C_{10})$-aryl or heterocycle;

R7 and R8 which independently of one another are selected from the group consisting of H, $(C_1$-$C_6)$-alkyl, —$CF_3$, $(C_3$-$C_{10})$-cycloalkyl, $(C_6$-$C_{10})$-aryl, heterocyclyl, $(C_1$-$C_6)$-alkylene-CONR9R10, CONR9R10, $(C_1$-$C_6)$-alkylene-COOR9, COOR9, COR9, $(C_1$-$C_6)$-alkylene-COR9, $(C_1$-$C_6)$-alkylene-OR9, $(C_1$-$C_6)$-alkylene-NR9R10, $(C_1$-$C_6)$-alkylene-SR9, $(C_1$-$C_6)$-alkylene-S(O)R9, $(C_1$-$C_6)$-alkylene-S(O)$_2$R9, S(O)R9, S(O)$_2$R9, $(C_1$-$C_4)$-alkylene-$(C_6$-$C_{10})$-aryl or $(C_1$-$C_4)$-alkylene-heterocycle;

R9 and R10 which independently of one another are selected from the group consisting of H, $(C_1$-$C_6)$-alkyl, $(C_1$-$C_6)$-alkylene-$(C_6$-$C_{10})$-aryl, —$(C_6$-$C_{10})$-aryl, heterocycle, $(C_1$-$C_6)$-alkylene-heterocycle, and;

R4 and R5 together form the group —$CH_2$—$CH_2$—NH—; and

R6 is H;

or the physiologically tolerated salt thereof.

Particularly preferred are the compounds of formula I in which one or more R groups are defined as follows:

R1 is $(C_1$-$C_{10})$-alkyl, wherein the alkyl group may be substituted by COR7;

R2 is $(C_1$-$C_{10})$-alkyl;

R3 is $(C_1$-$C_{10})$-alkyl, $(C_2$-$C_{10})$-alkenyl;

R7 is $(C_6$-$C_{10})$-aryl;

R4 and R5 together form the group —$CH_2$—$CH_2$—NH—; and

R6 is H;

or the physiologically tolerated salt thereof.

The invention also comprises compounds of the formula I in the form of their racemates, racemic mixtures, pure enantiomers, their diastereomers and mixtures thereof.

If the R-groups and other substituents occur more than once in the compounds of the formula I, they may all, independently of one another, consist of the prior defined carbon-based structures and may be identical or different.

Pharmaceutically acceptable salts are, because their solubility in water is greater than that of the initial or basic compounds and these are particularly suitable for medical applications. These salts must have a pharmaceutically acceptable anion or cation. Suitable pharmaceutically acceptable acid addition salts of the compounds of the invention are salts of inorganic acids such as hydrochloric acid, hydrobromic, phosphoric, metaphosphoric, nitric and sulfuric acid, and of organic acids such as, for example, acetic acid, benzenesulfonic, benzoic, citric, ethanesulfonic, fumaric, gluconic, glycolic, isethionic, lactic, lactobionic, maleic, malic, methanesulfonic, succinic, p-toluenesulfonic and tartaric acid. Suitable pharmaceutically acceptable basic salts are ammonium salts, alkali metal salts (such as sodium and potassium salts), alkaline earth metal salts (such as magnesium and calcium salts), trometamol (2-amino-2-hydroxymethyl-1,3-propanediol), diethanolamine, lysine or ethylenediamine.

Salts with a pharmaceutically unacceptable anion such as, for example, trifluoroacetate, likewise belong within the framework of the invention as useful intermediates for the preparation or purification of pharmaceutically acceptable salts and/or for use in non-therapeutic, for example in vitro, applications.

The term "physiologically functional derivative" used herein refers to any physiologically tolerated derivative of a compound of the formula I of the invention, for example an ester, which on administration to a mammal such as, for example, a human is able to form (directly or indirectly) a compound of the formula I or an active metabolite thereof.

Physiologically functional derivatives include prodrugs of the compounds of the invention. Such prodrugs can be metabolized in vivo to a compound of the invention. These prodrugs may themselves be active or not.

The compounds of the invention may also exist in various polymorphous forms, for example as amorphous and crystalline polymorphous forms. All polymorphous forms of the compounds of the invention belong within the framework of the invention and are a further aspect of the invention.

All references to "compound(s) of formula I" hereinafter refer to compound(s) of the formula I as described above, and their salts, solvates and physiologically functional derivatives as described herein.

An alkyl radical means a straight-chain or branched hydrocarbon chain having one or more carbons, such as, for example, methyl, ethyl, isopropyl, tert-butyl, or hexyl.

The alkyl radicals may be substituted one or more times by suitable groups such as, for example:

F, Cl, Br, I, $CF_3$, $NO_2$, $N_3$, CN, COOH, COO$(C_1$-$C_6)$alkyl, $CONH_2$, CONH$(C_1$-$C_6)$alkyl, CON$[(C_1$-$C_6)$alkyl]$_2$, cycloalkyl, $(C_2$-$C_6)$-alkenyl, $(C_2$-$C_6)$-alkynyl, O—$(C_1$-$C_6)$-alkyl O—CO—$(C_1$-$C_6)$-alkyl, O—CO—$(C_1$-$C_6)$-aryl, O—CO—$(C_1$-$C_6)$-heterocycle; $PO_3H_2$, $SO_3H$, $SO_2$—$NH_2$, $SO_2NH(C_1$-$C_6)$-alkyl, $SO_2N[(C_1$-$C_6)$-alkyl]$_2$, S—$(C_1$-$C_6)$-alkyl, S—$(CH_2)_n$-aryl, S—$(CH_2)$n-heterocycle, SO—($C_1$-$C_6$)-alkyl, SO—($CH_2$)$_n$-aryl, SO—($CH_2$)$_n$-heterocycle, $SO_2$—($C_1$-$C_6$)-alkyl, $SO_2$—($CH_2$)$_n$-aryl, $SO_2$—($CH_2$)$_n$-heterocycle, $SO_2$—NH($CH_2$)$_n$-aryl, $SO_2$—NH($CH_2$)$_n$-heterocycle, $SO_2$—N($C_1$-$C_6$)-alkyl($CH_2$)$_n$-aryl, $SO_2$—N($C_1$-$C_6$)-alkyl)($CH_2$)$_n$-heterocycle, $SO_2$—N(($CH_2$)$_n$-aryl)$_2$, $SO_2$—N(($CH_2$)$_n$-(heterocycle)$_2$ where n may be 0-6, and the aryl radical or heterocyclic radical may be substituted up to twice by F, Cl, Br, OH, $CF_3$, $NO_2$, CN, $OCF_3$, O—($C_1$-$C_6$)-alkyl, ($C_1$-$C_6$)-alkyl, $NH_2$; C(NH)($NH_2$), $NH_2$, NH—($C_1$-$C_6$)-alkyl, N(($C_1$-$C_6$)-alkyl)$_2$, NH($C_1$-$C_7$)-acyl, NH—CO—($C_1$-$C_6$)-alkyl, NH—COO—($C_1$-$C_6$)-alkyl, NH—CO-aryl, NH—CO-heterocycle, NH—COO-aryl, NH—COO-heterocycle, NH—CO—NH—($C_1$-$C_6$)-alkyl, NH—CO—NH-aryl, NH—CO—NH-heterocycle, N($C_1$-$C_6$)-alkyl —CO—($C_1$-$C_6$)-alkyl, N($C_1$-$C_6$)-alkyl-COO—($C_1$-$C_6$)-alkyl, N($C_1$-$C_6$)-alkyl —CO-aryl, N($C_1$-$C_6$)-alkyl —CO-heterocycle, N($C_1$-$C_6$)-alkyl —COO-aryl, N($C_1$-$C_6$)-alkyl —COO-heterocycle, N($C_1$-$C_6$)-alkyl —CO—NH—($C_1$-$C_6$)-alkyl), N($C_1$-$C_6$)-alkyl —CO—NH-aryl, N($C_1$-$C_6$)-alkyl —CO—NH-heterocycle, N(($C_1$-$C_6$)-alkyl)-CO—N—($C_1$-$C_6$)-alkyl)$_2$, N(($C_1$-$C_6$)-alkyl)-CO—N(($C_1$-$C_6$)-alkyl)-aryl, N(($C_1$-$C_6$)-alkyl)-CO—N(($C_1$-$C_6$)-alkyl)-heterocycle, N(($C_1$-$C_6$)-alkyl)-CO—N-(aryl)$_2$, N(($C_1$-$C_6$)-alkyl)-CO—N-(heterocycle)$_2$, N(aryl)-CO—($C_1$-$C_6$)-alkyl, N(heterocycle)-CO—($C_1$-$C_6$)-alkyl, N(aryl)-COO—($C_1$-$C_6$)-alkyl, N(heterocycle)-COO—($C_1$-$C_6$)-alkyl, N(aryl)-CO-aryl, N(heterocycle)-CO-aryl, N(aryl)-COO-aryl, N(heterocycle)-COO-aryl, N(aryl)-CO—NH—($C_1$-$C_6$)-alkyl), N(heterocycle)-CO—NH—($C_1$-$C_6$)-alkyl), N(aryl)-CO—NH-aryl, N(heterocycle)-CO—NH-aryl, N(aryl)-CO—N—($C_1$-$C_6$)-alkyl)$_2$, N(heterocycle)-CO—N—($C_1$-$C_6$)-alkyl)$_2$, N(aryl)-CO—N(($C_1$-$C_6$)-alkyl)-aryl, N(heterocycle)-CO—N(($C_1$-$C_6$)-alkyl)-aryl, N(aryl)-CO—N-(aryl)$_2$, N(heterocycle)-CO—N-(aryl)$_2$, aryl, O—($CH_2$)$_n$-aryl, O—($CH_2$)$_n$-heterocycle, where n may be 0-6, where the aryl radical or heterocyclic radical may be substituted one to 3 times by F, Cl, Br, I, OH, $CF_3$, $NO_2$, CN, $OCF_3$, O—($C_1$-$C_6$)-alkyl, ($C_1$-$C_6$)-alkyl, $NH_2$, NH($C_1$-$C_6$)-alkyl, N(($C_1$-$C_6$)-alkyl)$_2$, $SO_2$—$CH_3$, COOH, COO—($C_1$-$C_6$)-alkyl, $CONH_2$.

An alkenyl radical means a straight-chain or branched hydrocarbon chain having two or more carbons and one or more double bonds, such as, for example, vinyl, allyl, pentenyl, 2-methyl-but-2-en-4-yl.

The alkenyl radicals may be substituted one or more times by suitable groups such as, for example: F, Cl, Br, I, $CF_3$, $NO_2$, $N_3$, CN, COOH, COO($C_1$-$C_6$)alkyl, $CONH_2$, CONH($C_1$-$C_6$)alkyl, CON[($C_1$-$C_6$)alkyl]$_2$, cycloalkyl, ($C_1$-$C_{10}$)-alkyl, ($C_2$-$C_6$)-alkynyl, O—($C_1$-$C_6$)-alkyl O—CO—($C_1$-$C_6$)-alkyl, O—CO—($C_1$-$C_6$)-aryl, O—CO—($C_1$-$C_6$)-heterocycle; $PO_3H_2$, $SO_3H$, $SO_2$—$NH_2$, $SO_2NH$($C_1$-$C_6$)-alkyl, $SO_2N$[($C_1$-$C_6$)-alkyl]$_2$, S—($C_1$-$C_6$)-alkyl, S—($CH_2$)$_n$-aryl, S—($CH_2$)$_n$-heterocycle, SO—($C_1$-$C_6$)-alkyl, SO—($CH_2$)$_n$-aryl, SO—($CH_2$)$_n$-heterocycle, $SO_2$—($C_1$-$C_6$)-alkyl, $SO_2$—($CH_2$)$_n$-aryl, $SO_2$—($CH_2$)$_n$-heterocycle, $SO_2$—NH($CH_2$)$_n$-aryl, $SO_2$—NH($CH_2$)$_n$-heterocycle, $SO_2$—N($C_1$-$C_6$)-alkyl)($CH_2$)$_n$-aryl, $SO_2$—N($C_1$-$C_6$)-alkyl)($CH_2$)$_n$-heterocycle, $SO_2$—N(($CH_2$)$_n$-aryl)$_2$, $SO_2$—N(($CH_2$)$_n$-(heterocycle)$_2$ where n may be 0-6, and the aryl radical or heterocyclic radical may be substituted up to twice by F, Cl, Br, OH, $CF_3$, $NO_2$, CN, $OCF_3$, O—($C_1$-$C_6$)-alkyl, ($C_1$-$C_6$)-alkyl, $NH_2$; C(NH)($NH_2$), $NH_2$, NH—($C_1$-$C_6$)-alkyl, N(($C_1$-$C_6$)-alkyl)$_2$, NH($C_1$-$C_7$)-acyl, NH—CO—($C_1$-$C_6$)-alkyl, NH—COO—($C_1$-$C_6$)-alkyl, NH—CO-aryl, NH—CO-heterocycle, NH—COO-aryl, NH—COO-heterocycle, NH—CO—NH—($C_1$-$C_6$)-alkyl, NH—CO—NH-aryl, NH—CO—NH-heterocycle, N($C_1$-$C_6$)-alkyl —CO—($C_1$-$C_6$)-alkyl, N($C_1$-$C_6$)-alkyl —COO—($C_1$-$C_6$)-alkyl, N($C_1$-$C_6$)-alkyl —CO-aryl, N($C_1$-$C_6$)-alkyl —CO-heterocycle, N($C_1$-$C_6$)-alkyl —COO-aryl, N($C_1$-$C_6$)-alkyl —COO-heterocycle, N($C_1$-$C_6$)-alkyl —CO—NH—($C_1$-$C_6$)-alkyl), N($C_1$-$C_6$)-alkyl —CO—NH-aryl, N($C_1$-$C_6$)-alkyl —CO—NH-heterocycle, N(($C_1$-$C_6$)-alkyl)-CO—N—($C_1$-$C_6$)-alkyl)$_2$, N(($C_1$-$C_6$)-alkyl)-CO—N(($C_1$-$C_6$)-alkyl)-aryl, N(($C_1$-$C_6$)-alkyl)-CO—N(($C_1$-$C_6$)-alkyl)-heterocycle, N(($C_1$-$C_6$)-alkyl)-CO—N-(aryl)$_2$, N(($C_1$-$C_6$)-alkyl)-CO—N-(heterocycle)$_2$, N(aryl)-CO—($C_1$-$C_6$)-alkyl, N(heterocycle)-CO—($C_1$-$C_6$)-alkyl, N(aryl)-COO—($C_1$-$C_6$)-alkyl, N(heterocycle)-COO—($C_1$-$C_6$)-alkyl, N(aryl)-CO-aryl, N(heterocycle)-CO-aryl, N(aryl)-COO-aryl, N(heterocycle)-COO-aryl, N(aryl)-CO—NH—($C_1$-$C_6$)-alkyl), N(heterocycle)-CO—NH—($C_1$-$C_6$)-alkyl), N(aryl)-CO—NH-aryl, N(heterocycle)-CO—NH-aryl, N(aryl)-CO—N—($C_1$-$C_6$)-alkyl)$_2$, N(heterocycle)-CO—N—($C_1$-$C_6$)-alkyl)$_2$, N(aryl)-CO—N(($C_1$-$C_6$)-alkyl)-aryl, N(heterocycle)-CO—N(($C_1$-$C_6$)-alkyl)-aryl, N(aryl)-CO—N-(aryl)$_2$, N(heterocycle)-CO—N-(aryl)$_2$, aryl, O—($CH_2$)$_n$-aryl, O—($CH_2$)$_n$-heterocycle, where n may be 0-6, where the aryl radical or heterocyclic radical may be substituted one to 3 times by F, Cl, Br, I, OH, $CF_3$, $NO_2$, CN, $OCF_3$, O—($C_1$-$C_6$)-alkyl, ($C_1$-$C_6$)-alkyl, $NH_2$, NH($C_1$-$C_6$)-alkyl, N(($C_1$-$C_6$)-alkyl)$_2$, $SO_2$—$CH_3$, COOH, COO—($C_1$-$C_6$)-alkyl, $CONH_2$.

An alkynyl radical means a straight-chain or branched hydrocarbon chain having two or more carbons and one or more triple bonds, such as, for example, ethynyl, propynyl, butynyl, hexynyl.

The alkynyl radicals may be substituted one or more times by suitable groups such as, for example: F, Cl, Br, I, $CF_3$, $NO_2$, $N_3$, CN, COOH, COO($C_1$-$C_6$)alkyl, $CONH_2$, CONH($C_1$-$C_6$)alkyl, CON[($C_1$-$C_6$)alkyl]$_2$, cycloalkyl, ($C_2$-$C_6$)-alkenyl, ($C_1$-$C_{10}$)-alkyl, O—($C_1$-$C_6$)-alkyl O—CO—($C_1$-$C_6$)-alkyl, O—CO—($C_1$-$C_6$)-aryl, O—CO—($C_1$-$C_6$)-heterocycle; $PO_3H_2$, $SO_3H$, $SO_2$—$NH_2$, $SO_2NH$($C_1$-$C_6$)-alkyl, $SO_2N$[($C_1$-$C_6$)-alkyl]$_2$, S—($C_1$-$C_6$)-alkyl, S—($CH_2$)$_n$-aryl, S—($CH_2$)$_n$-heterocycle, SO—($C_1$-$C_6$)-alkyl, SO—($CH_2$)$_n$-aryl, SO—($CH_2$)$_n$-heterocycle, $SO_2$—($C_1$-$C_6$)-alkyl, $SO_2$—($CH_2$)$_n$-aryl, $SO_2$—($CH_2$)$_n$-heterocycle, $SO_2$—NH($CH_2$)$_n$-aryl, $SO_2$—NH($CH_2$)$_n$-heterocycle, $SO_2$—N($C_1$-$C_6$)-alkyl)($CH_2$)$_n$-aryl, $SO_2$—N($C_1$-$C_6$)-alkyl)($CH_2$)$_n$-heterocycle, $SO_2$—N(($CH_2$)$_n$-aryl)$_2$, $SO_2$—N(($CH_2$)$_n$-(heterocycle)$_2$ where n may be 0-6, and the aryl radical or heterocyclic radical may be substituted up to twice by F, Cl, Br, OH, $CF_3$, $NO_2$, CN, $OCF_3$, O—($C_1$-$C_6$)-alkyl, ($C_1$-$C_6$)-alkyl, $NH_2$; C(NH)($NH_2$), $NH_2$, NH—($C_1$-$C_6$)-alkyl, N(($C_1$-$C_6$)-alkyl)$_2$, NH($C_1$-$C_7$)-acyl, NH—CO—($C_1$-$C_6$)-alkyl, NH—COO—($C_1$-$C_6$)-alkyl, NH—CO-aryl, NH—CO-heterocycle, NH—COO-aryl, NH—COO-heterocycle, NH—CO—NH—($C_1$-$C_6$)-alkyl, NH—CO—NH-aryl, NH—CO—NH-heterocycle, N($C_1$-$C_6$)-alkyl —CO—($C_1$-$C_6$)-alkyl, N($C_1$-$C_6$)-alkyl —COO—($C_1$-$C_6$)-alkyl, N($C_1$-$C_6$)-alkyl —CO-aryl, N($C_1$-$C_6$)-alkyl —CO-heterocycle, N($C_1$-$C_6$)-alkyl —COO-aryl, N($C_1$-$C_6$)-alkyl —COO-heterocycle, N($C_1$-$C_6$)-alkyl —CO—NH—($C_1$-$C_6$)-alkyl), N($C_1$-$C_6$)-alkyl —CO—NH-aryl, N($C_1$-$C_6$)-alkyl —CO—NH-heterocycle, N(($C_1$-$C_6$)-alkyl)-CO—N—($C_1$-$C_6$)-alkyl)$_2$, N(($C_1$-$C_6$)-alkyl)-CO—N(($C_1$-$C_6$)-alkyl)-aryl, N(($C_1$-$C_6$)-alkyl)-CO—N(($C_1$-$C_6$)-alkyl)-heterocycle, N(($C_1$-$C_6$)-alkyl)-CO—N-(aryl)$_2$, N(($C_1$-$C_6$)-alkyl)-CO—N-(heterocycle)$_2$, N(aryl)-CO—($C_1$-$C_6$)-alkyl, N(heterocycle)-CO—($C_1$-$C_6$)-alkyl, N(aryl)-

COO—($C_1$-$C_6$)-alkyl, N(heterocycle)-COO—($C_1$-$C_6$)-alkyl, N(aryl)-CO-aryl, N(heterocycle)-CO-aryl, N(aryl)-COO-aryl, N(heterocycle)-COO-aryl, N(aryl)-CO—NH—($C_1$-$C_6$)-alkyl), N(heterocycle)-CO—NH—($C_1$-$C_6$)-alkyl), N(aryl)-CO—NH-aryl, N(heterocycle)-CO—NH-aryl, N(aryl)-CO—N—($C_1$-$C_6$)-alkyl)$_2$, N(heterocycle)-CO—N—($C_1$-$C_6$)-alkyl)$_2$, N(aryl)-CO—N(($C_1$-$C_6$)-alkyl)-aryl, N(heterocycle)-CO—N(($C_1$-$C_6$)-alkyl)-aryl, N(aryl)-CO—N-(aryl)$_2$, N(heterocycle)-CO—N-(aryl)$_2$, aryl, O—($CH_2$)$_n$-aryl, O—($CH_2$)$_n$-heterocycle, where n may be 0-6, where the aryl radical or heterocyclic radical may be substituted one to 3 times by F, Cl, Br, I, OH, $CF_3$, $NO_2$, CN, $OCF_3$, O—($C_1$-$C_6$)-alkyl, ($C_1$-$C_6$)-alkyl, $NH_2$, NH($C_1$-$C_6$)-alkyl, N(($C_1$-$C_6$)-alkyl)$_2$, $SO_2$—$CH_3$, COOH, COO—($C_1$-$C_6$)-alkyl, $CONH_2$.

Aryl means a phenyl, naphthyl-, biphenyl, tetrahydronaphthyl-, alpha- or beta- tetralon-, indanyl- or indan-1-on-yl radical.

The aryl groups may be substituted one or more times by suitable halogens, amines elements and moieties such as, for example: F, Cl, Br, I, $CF_3$, $NO_2$, $N_3$, CN, COOH, COO($C_1$-$C_6$)alkyl, $CONH_2$, CONH($C_1$-$C_6$)alkyl, CON[($C_1$-$C_6$)alkyl]$_2$ cycloalkyl, ($C_1$-$C_{10}$)-alkyl, ($C_2$-$C_6$)-alkenyl, ($C_2$-$C_6$)-alkynyl, O—($C_1$-$C_6$)-alkyl O—CO—($C_1$-$C_6$)-alkyl, O—CO—($C_1$-$C_6$)-aryl, O—CO—($C_1$-$C_6$)-heterocycle;

$PO_3H_2$, $SO_3H$, $SO_2$—$NH_2$, $SO_2NH$($C_1$-$C_6$)-alkyl, $SO_2N$[($C_1$-$C_6$)-alkyl]$_2$, S—($C_1$-$C_6$)-alkyl, S—($CH_2$)$_n$-aryl, S—($CH_2$)$_n$-heterocycle, SO—($C_1$-$C_6$)-alkyl, SO—($CH_2$)$_n$-aryl, SO—($CH_2$)$_n$-heterocycle, $SO_2$—($C_1$-$C_6$)-alkyl, $SO_2$—($CH_2$)$_n$-aryl, $SO_2$—($CH_2$)$_n$-heterocycle, $SO_2$—NH($CH_2$)$_n$-aryl, $SO_2$—NH($CH_2$)$_n$-heterocycle, $SO_2$—N($C_1$-$C_6$)-alkyl)($CH_2$)$_n$-aryl, $SO_2$—N($C_1$-$C_6$)-alkyl)($CH_2$)$_n$-heterocycle, $SO_2$—N(($CH_2$)$_n$-aryl)$_2$, $SO_2$—N(($CH_2$)$_n$-(heterocycle)$_2$ where n may be 0-6, and the aryl radical or heterocyclic radical may be substituted up to twice by F, Cl, Br, OH, $CF_3$, $NO_2$, CN, $OCF_3$, O—($C_1$-$C_6$)-alkyl, ($C_1$-$C_6$)-alkyl, $NH_2$; C(NH)($NH_2$), $NH_2$, NH—($C_1$-$C_6$)-alkyl, N(($C_1$-$C_6$)-alkyl)$_2$, NH($C_1$-$C_7$)-acyl, NH—CO—($C_1$-$C_6$)-alkyl, NH—COO—($C_1$-$C_6$)-alkyl, NH—CO-aryl, NH—CO-heterocycle, NH—COO-aryl, NH—COO-heterocycle, NH—CO—NH—($C_1$-$C_6$)-alkyl, NH—CO—NH-aryl, NH—CO—NH-heterocycle, N($C_1$-$C_6$)-alkyl —CO—($C_1$-$C_6$)-alkyl, N($C_1$-$C_6$)-alkyl—COO—($C_1$-$C_6$)-alkyl, N($C_1$-$C_6$)-alkyl —CO-aryl, N($C_1$-$C_6$)-alkyl —CO-heterocycle, N($C_1$-$C_6$)-alkyl —COO-aryl, N($C_1$-$C_6$)-alkyl —COO-heterocycle, N($C_1$-$C_6$)-alkyl —CO—NH—($C_1$-$C_6$)-alkyl), N($C_1$-$C_6$)-alkyl —CO—NH-aryl, N($C_1$-$C_6$)-alkyl —CO—NH-heterocycle, N(($C_1$-$C_6$)-alkyl)-CO—N—($C_1$-$C_6$)-alkyl)$_2$, N(($C_1$-$C_6$)-alkyl)-CO—N(($C_1$-$C_6$)-alkyl)-aryl, N(($C_1$-$C_6$)-alkyl)-CO—N(($C_1$-$C_6$)-alkyl)-heterocycle, N(($C_1$-$C_6$)-alkyl)-CO—N-(aryl)$_2$, N(($C_1$-$C_6$)-alkyl)-CO—N-(heterocycle)$_2$, N(aryl)-CO—($C_1$-$C_6$)-alkyl, N(heterocycle)-CO—($C_1$-$C_6$)-alkyl, N(aryl)-COO—($C_1$-$C_6$)-alkyl, N(heterocycle)-COO—($C_1$-$C_6$)-alkyl, N(aryl)-CO-aryl, N(heterocycle)-CO-aryl, N(aryl)-COO-aryl, N(heterocycle)-COO-aryl, N(aryl)-CO—NH—($C_1$-$C_6$)-alkyl), N(heterocycle)-CO—NH—($C_1$-$C_6$)-alkyl), N(aryl)-CO—NH-aryl, N(heterocycle)-CO—NH-aryl, N(aryl)-CO—N—($C_1$-$C_6$)-alkyl)$_2$, N(heterocycle)-CO—N—($C_1$-$C_6$)-alkyl)$_2$, N(aryl)-CO—N(($C_1$-$C_6$)-alkyl)-aryl, N(heterocycle)-CO—N(($C_1$-$C_6$)-alkyl)-aryl, N(aryl)-CO—N-(aryl)$_2$, N(heterocycle)-CO—N-(aryl)$_2$, aryl, O—($CH_2$)$_n$-aryl, O—($CH_2$)$_n$-heterocycle, where n may be 0-6, where the aryl radical or heterocyclic radical may be substituted one to 3 times by F, Cl, Br, I, OH, $CF_3$, $NO_2$, CN, $OCF_3$, O—($C_1$-$C_6$)-alkyl, ($C_1$-$C_6$)-alkyl, $NH_2$, NH($C_1$-$C_6$)-alkyl, N(($C_1$-$C_6$)-alkyl)$_2$, $SO_2$—$CH_3$, COOH, COO—($C_1$-$C_6$)-alkyl, $CONH_2$.

Cycloalkyl means a ring system which comprises one or more rings, which is in saturated or partially unsaturated (with one or two double bonds) form and which is composed exclusively of carbon atoms, such as, for example, cyclopropyl, cyclopentyl, cyclopentenyl, cyclohexyl or adamantyl.

The cycloalkyl groups may be substituted one or more times by groups such as halogens, amines elements and moieties such as, for example: F, Cl, Br, I, $CF_3$, $NO_2$, $N_3$, CN, COOH, COO($C_1$-$C_6$)alkyl, $CONH_2$, CONH($C_1$-$C_6$)alkyl, CON[($C_1$-$C_6$)alkyl]$_2$, cycloalkyl, ($C_1$-$C_{10}$)-alkyl, ($C_2$-$C_6$)-alkenyl, ($C_2$-$C_6$)-alkynyl, O—($C_1$-$C_6$)-alkyl O—CO—($C_1$-$C_6$)-alkyl, O—CO—($C_1$-$C_6$)-aryl, O—CO—($C_1$-$C_6$)-heterocycle; $PO_3H_2$, $SO_3H$, $SO_2$—$NH_2$, $SO_2NH$($C_1$-$C_6$)-alkyl, $SO_2N$[($C_1$-$C_6$)-alkyl]$_2$, S—($C_1$-$C_6$)-alkyl, S—($CH_2$)n-aryl, S—($CH_2$)n-heterocycle, SO—($C_1$-$C_6$)-alkyl, SO—($CH_2$)n-aryl, SO—($CH_2$)$_n$-heterocycle, $SO_2$—($C_1$-$C_6$)-alkyl, $SO_2$—($CH_2$)$_n$-aryl, $SO_2$—($CH_2$)$_n$-heterocycle, $SO_2$—NH($CH_2$)n-aryl, $SO_2$—N(($CH_2$)n-heterocycle, $SO_2$—N($C_1$-$C_6$)-alkyl)($CH_2$)$_n$-aryl, $SO_2$—N($C_1$-$C_6$)-alkyl)($CH_2$)$_n$-heterocycle, $SO_2$—N(($CH_2$)$_n$-aryl)$_2$, $SO_2$—N(($CH_2$)$_n$-(heterocycle)$_2$ where n may be 0-6, and the aryl radical or heterocyclic radical may be substituted up to twice by F, Cl, Br, OH, $CF_3$, $NO_2$, CN, $OCF_3$, O—($C_1$-$C_6$)-alkyl, ($C_1$-$C_6$)-alkyl, $NH_2$; C(NH)($NH_2$), $NH_2$, NH—($C_1$-$C_6$)-alkyl, N(($C_1$-$C_6$)-alkyl)$_2$, NH($C_1$-$C_7$)-acyl, NH—CO—($C_1$-$C_6$)-alkyl, NH—COO—($C_1$-$C_6$)-alkyl, NH—CO-aryl, NH—CO-heterocycle, NH—COO-aryl, NH—COO-heterocycle, NH—CO—NH—($C_1$-$C_6$)-alkyl, NH—CO—NH-aryl, NH—CO—NH-heterocycle, N($C_1$-$C_6$)-alkyl —CO—($C_1$-$C_6$)-alkyl, N($C_1$-$C_6$)-alkyl-COO—($C_1$-$C_6$)-alkyl, N($C_1$-$C_6$)-alkyl-CO-aryl, N($C_1$-$C_6$)-alkyl-CO-heterocycle, N($C_1$-$C_6$)-alkyl-COO-aryl, N($C_1$-$C_6$)-alkyl-COO-heterocycle, N($C_1$-$C_6$)-alkyl-CO—NH—($C_1$-$C_6$)-alkyl), N($C_1$-$C_6$)-alkyl-CO—NH-aryl, N($C_1$-$C_6$)-alkyl-CO—NH-heterocycle, N(($C_1$-$C_6$)-alkyl)-CO—N—($C_1$-$C_6$)-alkyl)$_2$, N(($C_1$-$C_6$)-alkyl)-CO—N(($C_1$-$C_6$)-alkyl)-aryl, N(($C_1$-$C_6$)-alkyl)-CO—N(($C_1$-$C_6$)-alkyl)-heterocycle, N(($C_1$-$C_6$)-alkyl)-CO—N-(aryl)$_2$, N(($C_1$-$C_6$)-alkyl)-CO—N-(heterocycle)$_2$, N(aryl)-CO—($C_1$-$C_6$)-alkyl, N(heterocycle)-CO—($C_1$-$C_6$)-alkyl, N(aryl)-COO—($C_1$-$C_6$)-alkyl, N(heterocycle)-COO—($C_1$-$C_6$)-alkyl, N(aryl)-CO-aryl, N(heterocycle)-CO-aryl, N(aryl)-COO-aryl, N(heterocycle)-COO-aryl, N(aryl)-CO—NH—($C_1$-$C_6$)-alkyl), N(heterocycle)-CO—NH—($C_1$-$C_6$)-alkyl), N(aryl)-CO—NH-aryl, N(heterocycle)-CO—NH-aryl, N(aryl)-CO—N—($C_1$-$C_6$)-alkyl)$_2$, N(heterocycle)-CO—N—($C_1$-$C_6$)-alkyl)$_2$, N(aryl)-CO—N(($C_1$-$C_6$)-alkyl)-aryl, N(heterocycle)-CO—N(($C_1$-$C_6$)-alkyl)-aryl, N(aryl)-CO—N-(aryl)$_2$, N(heterocycle)-CO—N-(aryl)$_2$, aryl, O—($CH_2$)$_n$-aryl, O—($CH_2$)$_n$-heterocycle, where n may be 0-6, where the aryl radical or heterocyclic radical may be substituted one to 3 times by F, Cl, Br, I, OH, $CF_3$, $NO_2$, CN, $OCF_3$, O—($C_1$-$C_6$)-alkyl, ($C_1$-$C_6$)-alkyl, $NH_2$, NH($C_1$-$C_6$)-alkyl, N(($C_1$-$C_6$)-alkyl)$_2$, $SO_2$—$CH_3$, COOH, COO—($C_1$-$C_6$)-alkyl, $CONH_2$.

Heterocycle or heterocyclic groups are rings and ring systems which, apart from carbon, also comprise heteroatoms such as, for example, nitrogen, oxygen or sulfur. Also included in this definition are ring systems in which the heterocycle or the heterocyclic group is fused to benzene nuclei. The heterocycle or the heterocyclic group may be aromatic, saturated aliphatic or partially unsaturated aliphatic.

Suitable heterocyclic rings are acridinyl, azocinyl, benzimidazolyl, benzofuryl, benzothienyl, benzothiophenyl, benzoxazolyl, benzthiazolyl, benztriazolyl, benztetrazolyl, benzisoxazolyi, benzisothiazolyl, benzimidazalinyl, carbazolyl, 4aH-carbazolyl, carbolinyl, quinazolinyl, quinolinyl, 4H-quinolizinyl, quinoxalinyl, quinuclidinyl, chromanyl, chromenyl, cinnolinyl, decahydroquinolinyl, 2H,6H-1,5,2-dithiazinyl, dihydrofuro[2,3-b]-tetrahydrofuran, furyl, furazanyl, imidazolidinyl, imidazolinyl, imidazolyl, 1H-indazolyl, indolinyl, indolizinyl, indolyl, 3H-indolyl, isobenzofuranyl, isochromanyl, isoindazolyl, isoindolinyl, isoindolyl, isoquinolinyl (benzimidazolyl), isothiazolyl, isoxazolyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxazolidinyl, pyrimidinyl, phenanthridinyl, phenanthrolinyl, phenazinyl, phenothiazinyl, phenoxathiinyl, phenoxazinyl, phthalazinyl, piperazinyl, piperidinyl, pteridinyl, purynyl, pyranyl, pyrazinyl, pyroazolidinyl, pyrazolinyl, pyrazolyl, pyridazinyl, pyridooxazoles, pyridoimidazoles, pyridothiazoles, pyridinyl, pyridyl, pyrimidinyl, pyrrolidinyl, pyrrolinyl, 2H-pyrrolyl, pyrrolyl, tetrahydrofuranyl, tetrahydroisoquinolinyl, tetrahydroquinolinyl, 6H-1,2,5-thiadazinyl, thiazolyl, 1,2,3-thiadiazolyl, 1,2,4-thiadiazolyi, 1,2,5-thiadiazolyl, 1,3,4-thiadiazolyl, thienyl, triazolyl, tetrazolyl and xanthenyl.

Pyridyl groups may be 2-, 3- and 4-pyridyl. Thienyl stands both for 2- and 3-thienyl. Furyl stands both for 2- and 3-furyl.

Also included are the corresponding N-oxides of these compounds, that is to say, for example, 1-oxy-2-, 3- or 4-pyridyl.

Also included are derivatives of these heterocycles which are benzo-fused one or more times.

The heterocyclic rings may be substituted one or more times by suitable groups such as, for example: F, Cl, Br, I, $CF_3$, $NO_2$, $N_3$, CN, COOH, COO($C_1$-$C_6$)alkyl, $CONH_2$, $CONH(C_1$-$C_6)$alkyl, $CON[(C_1$-$C_6)$alkyl$]_2$, cycloalkyl, ($C_1$-$C_{10}$)-alkyl, ($C_2$-$C_6$)-alkenyl, ($C_2$-$C_6$)-alkynyl, O—($C_1$-$C_6$)-alkyl O—CO—($C_1$-$C_6$)-alkyl, O—CO—($C_1$-$C_6$)-aryl, O—CO—($C_1$-$C_6$)-heterocycle;

$PO_3H_2$, $SO_3H$, $SO_2$—$NH_2$, $SO_2NH(C_1$-$C_6)$-alkyl, $SO_2N[(C_1$-$C_6)$-alkyl$]_2$, S—($C_1$-$C_6$)-alkyl, S—($CH_2)_n$-aryl, S—($CH_2)_n$-heterocycle, SO—($C_1$-$C_6$)-alkyl, SO—($CH_2)_n$-aryl, SO—($CH_2)_n$-heterocycle, $SO_2$—($C_1$-$C_6$)-alkyl, $SO_2$—($CH_2)_n$-aryl, $SO_2$—($CH_2)_n$-heterocycle, $SO_2$—$NH(CH_2)_n$-aryl, $SO_2$—$NH(CH_2)_n$-heterocycle, $SO_2$—$N(C_1$-$C_6)$-alkyl)($CH_2)_n$-aryl, $SO_2$—$N(C_1$-$C_6)$-alkyl)($CH_2)_n$-heterocycle, $SO_2$—$N((CH_2)_n$-aryl$)_2$, $SO_2$—$N((CH_2)_n$-(heterocycle)$_2$ where n may be 0-6, and the aryl radical or heterocyclic radical may be substituted up to twice by F, Cl, Br, OH, $CF_3$, $NO_2$, CN, $OCF_3$, O—($C_1$-$C_6$)-alkyl, ($C_1$-$C_6$)-alkyl, $NH_2$; $C(NH)(NH_2)$, $NH_2$, NH—($C_1$-$C_6$)-alkyl, $N((C_1$-$C_6)$-alkyl$)_2$, $NH(C_1$-$C_7)$-acyl, NH—CO—($C_1$-$C_6$)-alkyl, NH—COO—($C_1$-$C_6$)-alkyl, NH—CO-aryl, NH—CO-heterocycle, NH—COO-aryl, NH—COO-heterocycle, NH—CO—NH—($C_1$-$C_6$)-alkyl, NH—CO—NH-aryl, NH—CO—NH-heterocycle, $N(C_1$-$C_6)$-alkyl-CO—($C_1$-$C_6$)-alkyl, $N(C_1$-$C_6)$-alkyl-COO—($C_1$-$C_6$)-alkyl, $N(C_1$-$C_6)$-alkyl-CO-aryl, $N(C_1$-$C_6)$-alkyl-CO-heterocycle, $N(C_1$-$C_6)$-alkyl-COO-aryl, $N(C_1$-$C_6)$-alkyl-COO-heterocycle, $N(C_1$-$C_6)$-alkyl-CO—NH—($C_1$-$C_6$)-alkyl), $N(C_1$-$C_6)$-alkyl-CO—NH-aryl, $N(C_1$-$C_6)$-alkyl-CO—NH-heterocycle, $N((C_1$-$C_6)$-alkyl)-CO—N—($C_1$-$C_6$)-alkyl$)_2$, $N((C_1$-$C_6)$-alkyl)-CO—$N((C_1$-$C_6)$-alkyl)-aryl, $N((C_1$-$C_6)$-alkyl)-CO—$N((C_1$-$C_6)$-alkyl)-heterocycle, $N((C_1$-$C_6)$-alkyl)-CO—N-(aryl$)_2$, $N((C_1$-$C_6)$-alkyl)-CO—N-(heterocycle$)_2$, N(aryl)-CO—($C_1$-$C_6$)-alkyl, N(heterocycle)-CO—($C_1$-$C_6$)-alkyl, N(aryl)-COO—($C_1$-$C_6$)-alkyl, N(heterocycle)-COO—($C_1$-$C_6$)-alkyl, N(aryl)-CO-aryl, N(heterocycle)-CO-aryl, N(aryl)-COO-aryl, N(heterocycle)-COO-aryl, N(aryl)-CO—NH—($C_1$-$C_6$)-alkyl), N(heterocycle)-CO—NH—($C_1$-$C_6$)-alkyl), N(aryl)-CO—NH-aryl, N(heterocycle)-CO—NH-aryl, N(aryl)-CO—N—($C_1$-$C_6$)-alkyl$)_2$, N(heterocycle)-CO—N—($C_1$-$C_6$)-alkyl$)_2$, N(aryl)-CO—$N((C_1$-$C_6)$-alkyl)-aryl, N(heterocycle)-CO—$N((C_1$-$C_6)$-alkyl)-aryl, N(aryl)-CO—N-(aryl$)_2$, N(heterocycle)-CO—N-(aryl$)_2$, aryl, O—($CH_2)_n$-aryl, O—($CH_2)_n$-heterocycle, where n may be 0-6, where the aryl radical or heterocyclic radical may be substituted one to 3 times by F, Cl, Br, I, OH, $CF_3$, $NO_2$, CN, $OCF_3$, O—($C_1$-$C_6$)-alkyl, ($C_1$-$C_6$)-alkyl, $NH_2$, $NH(C_1$-$C_6)$-alkyl, $N((C_1$-$C_6)$-alkyl$)_2$, $SO_2$—$CH_3$, COOH, COO—($C_1$-$C_6$)-alkyl, $CONH_2$.

The compound(s) of the formula (I) may also be administered in combination with additional active ingredients.

The amount of a compound of formula I necessary to achieve the desired biological effect depends on a number of factors, for example the specific compound chosen, the intended use, the mode of administration and the clinical condition of the patient. The daily dose is generally in the range from 0.3 mg to 100 mg (typically from 3 mg and 50 mg) per day and per kilogram of bodyweight, for example 3-10 mg/kg/day. An intravenous dose may be, for example, in the range from 0.3 mg to 1.0 mg/kg, which can suitably be administered as infusion of 10 ng to 100 ng per kilogram and per minute. Suitable infusion solutions for these purposes may contain, for example, from 0.1 ng to 10 mg, typically from 1 ng to 10 mg, per milliliter. Single doses may contain, for example, from 1 mg to 10 g of the active ingredient. Thus, ampoules for injections may contain, for example, from 1 mg to 100 mg, and single-dose formulations which can be administered orally, such as, for example, capsules or tablets, may contain, for example, from 1.0 to 1000 mg, typically from 10 to 600 mg. For the therapy of the abovementioned conditions, the compounds of formula I may be used as the compound itself, but they are preferably in the form of a pharmaceutical composition with an acceptable carrier. The carrier must, of course, be acceptable in the sense that it is compatible with the other ingredients of the composition and is not harmful for the patient's health. The carrier may be a solid or a liquid or both and is preferably formulated with the compound as a single dose, for example as a tablet, which may contain from 0.05% to 95% by weight of the active ingredient. Other pharmaceutically active substances may likewise be present, including other compounds of formula I. The pharmaceutical compositions of the invention can be produced by one of the known pharmaceutical methods, which essentially consist of mixing the ingredients with pharmacologically acceptable carriers and/or excipients.

Pharmaceutical compositions of the invention are those suitable for oral, rectal, topical, peroral (for example sublingual) and parenteral (for example subcutaneous, intramuscular, intradermal or intravenous) administration, although the most suitable mode of administration depends in each individual case on the nature and severity of the condition to be treated and on the nature of the compound of formula I used in each case. Coated formulations and coated slow-release formulations also belong within the framework of the invention. Preference is given to acid- and gastric juice-resistant formulations. Suitable coatings resistant to gastric juice comprise cellulose acetate phthalate, polyvinyl acetate phthalate, hydroxypropylmethylcellulose phthalate and anionic polymers of methacrylic acid and methyl methacrylate.

Suitable pharmaceutical compounds for oral administration may be in the form of separate units such as, for example, tablets, capsules, cachets, lozenges, chewable tablets each of which contain a defined amount of the compound of formula I; as powders or granules, as solution or suspension in an aqueous or non-aqueous liquid; or as an oil-in-water or water-in-oil emulsion. These compositions may, as already mentioned, be prepared by any suitable pharmaceutical method which includes a step in which the active ingredient and the carrier (which may consist of one or more additional ingredients) are brought into contact. The compositions are generally produced by uniform and homogeneous mixing of the active ingredient with a liquid and/or finely divided solid carrier, after which the product is shaped if necessary. Thus, for example, a tablet can be produced by compressing or molding a powder or granules of the compound, where appropriate with one or more additional ingredients. Compressed tablets can be produced by tableting the compound in free-flowing form such as, for example, a powder or granules, where appropriate mixed with a binder, glidant, inert diluent and/or one or more surface-active/dispersing agent(s) in a suitable machine. Molded tablets can be produced by molding the compound, which is in powder form and is moistened with an inert liquid diluent, in a suitable machine.

Pharmaceutical compositions which are suitable for peroral (sublingual) administration comprise slow-dissolving lozenges which contain a compound of formula I with a flavoring, normally sucrose and gum arabic or tragacanth, and pastilles which comprise the compound in an inert base such as gelatin and glycerol or sucrose and gum arabic.

Pharmaceutical compositions suitable for parenteral administration comprise preferably sterile aqueous preparations of a compound of formula I, which are preferably isotonic with the blood of the intended recipient. These preparations are preferably administered intravenously, although administration may also take place by subcutaneous, intramuscular or intradermal injection. These preparations can preferably be produced by mixing the compound with water and making the resulting solution sterile and isotonic with blood. Injectable compositions of the invention generally contain from 0.1 to 5% by weight of the active compound.

Pharmaceutical compositions suitable for rectal administration are preferably in the form of single-dose suppositories. These can be produced by mixing a compound of the formula I with one or more conventional solid carriers, for example cocoa butter, and shaping the resulting mixture.

Pharmaceutical compositions suitable for topical use on the skin are preferably in the form of ointment, cream, lotion, paste, spray, aerosol or oil. Carriers which can be used are petrolatum, lanolin, polyethylene glycols, alcohols and combinations of two or more of these substances. The active ingredient is generally present in a concentration of from 0.1 to 15% by weight of the composition, for example from 0.5 to 2%.

Transdermal administration is also possible. Pharmaceutical compositions suitable for transdermal uses can be in the form of single patches which are suitable for long-term close contact with the patient's epidermis. Such patches suitably contain the active ingredient in an aqueous solution which is buffered where appropriate, dissolved and/or dispersed in an adhesive or dispersed in a polymer. A suitable active ingredient concentration is about 1% to 35%, preferably about 3% to 15%. A particular possibility is for the active ingredient to be released by electrotransport or iontophoresis as described, for example, in Pharmaceutical Research, 2(6): 318 (1986), which is hereby incorporated by reference.

Further active ingredients suitable for combination products are for example, the antidiabetic compounds mentioned in the Rote Liste 2004, chapter 12. They may be combined with the compounds of the formula I of the invention in particular for a synergistic improvement of the effect. Administration of the active ingredient combination may take place either by separate administration of the active ingredients to the patient or in the form of combination products in which a plurality of active ingredients are present in one pharmaceutical preparation. Most of the active ingredients listed below are disclosed in the USP Dictionary of USAN and International Drug Names, US Pharmacopeia, Rockville 2001.

Antidiabetic agents include insulin and insulin derivatives such as, for example, Lantus® (see www.lantus.com) or fast-acting insulins, see for example, U.S. Pat. No. 6,221,633 to Ertle et. al. which discloses and claims asparagine-substituted insulin compounds., GLP-1 derivatives such as, for example, those disclosed in WO 98/08871 of Novo Nordisk A/S, and orally effective hypoglycemic active ingredients.

The orally effective hypoglycemic active ingredients include, preferably, sulfonylureas, bisguanidines, meglitinides, oxadiazolidinediones, thiazolidinediones, glucosidase inhibitors, glucagon antagonists, GLP-1 agonists, potassium channel openers such as, for example, those disclosed in WO 97/26265 and WO 99/03861 of Novo Nordisk A/S, insulin sensitizers, inhibitors of liver enzymes involved in the stimulation of gluconeogenesis and/or glycogenolysis, modulators of glucose uptake, compounds which alter lipid metabolism, such as antihyperlipidemic active ingredients and antilipidemic active ingredients, compounds which reduce food intake, PPAR and PXR agonists and active ingredients which act on the ATP-dependent potassium channel of the beta cells.

In another embodiment of the invention, the compounds of the formula I are administered in combination with an HMG-CoA reductase inhibitor such as simvastatin, fluvastatin, pravastatin, lovastatin, atorvastatin, cerivastatin, rosuvastatin.

In yet another embodiment of the invention, the compounds of the formula I are administered in combination with a cholesterol absorption inhibitor such as, for example, ezetimibe, tiqueside, pamaqueside, or with a compound as described in PCT/EP 2004/00269, PCT/EP 2003/05815, PCT/EP 2003/05814, PCT/EP 2003/05816, EP 0114531, U.S. Pat. No. 6,498,156 to Glompic et. al. which teaches and claims diphenylazetidinone derivatives as hyperlipidemic agents.

In one embodiment of the invention, the compounds of the formula I are administered in combination with a PPAR gamma agonist, such as, for example, rosiglitazone, pioglitazone, JTT-501, GI 262570.

In one embodiment of the invention, the compounds of the formula I are administered in combination with a PPAR alpha agonist, such as, for example, GW 9578, GW 7647.

In another possible embodiment of the present invention the compounds of the formula I are administered in combination rimonabant.

mazindol or phentermine embodiment of the invention, the compounds of the formula I are administered in combination with a mixed PPAR alpha/gamma agonist, such as, for example, GW 1536, AVE 8042, AVE 8134, AVE 0847, or as described in PCT/US 11833, PCT/US 11490, DE10142734.4.

In one embodiment of the invention, the compounds of the formula I are administered in combination with a fibrate such as, for example, fenofibrate, clofibrate, bezafibrate.

In one embodiment of the invention, the compounds of the formula I are administered in combination with an MTP inhibitor such as, for example, implitapide, BMS-201038, R-103757.

In one embodiment of the invention, the compounds of the formula I are administered in combination with bile acid absorption inhibitor such as, for example, HMR 1741 (see, for example, U.S. Pat. Nos. 6,245,744 and 6,221,897 to Frick et. al.), In one embodiment of the invention, the compounds of the formula I are administered in combination with a CETP inhibitor, such as, for example, JTT-705.

In one embodiment of the invention, the compounds of the formula I are administered in combination with a polymeric bile acid adsorbent such as, for example, cholestyramine, colesevelam.

In one embodiment of the invention, the compounds of the formula I are administered in combination with an LDL receptor inducer such as, for example, HMR1171, HMR1586 (see U.S. Pat. No. 6,342,512 to kirsch et. al.), In one embodiment of the invention, the compounds of the formula I are administered in combination with an ACAT inhibitor, such as, for example, avasimibe.

In one embodiment of the invention, the compounds of the formula I are administered in combination with an antioxidant, such as, for example, OPC-14117.

In one embodiment of the invention, the compounds of the formula I are administered in combination with a lipoprotein lipase inhibitor, such as, for example, NO-1886.

In one embodiment of the invention, the compounds of the formula I are administered in combination with an ATP-citrate lyase inhibitor, such as, for example, SB-204990.

In one embodiment of the invention, the compounds of the formula I are administered in combination with a squalene synthetase inhibitor, such as, for example, BMS-188494.

In one embodiment of the invention, the compounds of the formula I are administered in combination with a lipoprotein (a) antagonist, such as, for example, CI-1027 or nicotinic acid.

In one embodiment of the invention, the compounds of the formula I are administered in combination with a lipase inhibitor, such as, for example, orlistat.

In one embodiment of the invention, the compounds of the formula I are administered in combination with insulin.

In one embodiment, the compounds of the formula I are administered in combination with a sulfonylurea such as, for example, tolbutamide, glibenclamide, glipizide or glimepiride.

In one embodiment, the compounds of the formula I are administered in combination with a biguanide, such as, for example, metformin.

In one further embodiment, the compounds of the formula I are administered in combination with a meglitinide, such as, for example, repaglinide.

In one embodiment, the compounds of the formula I are administered in combination with a thiazolidinedione, such as, for example, troglitazone, ciglitazone, pioglitazone, rosiglitazone or the compounds disclosed in WO 97/41097 of Dr. Reddy's Research Foundation, in particular 5-[[4-[(3,4-dihydro-3-methyl-4-oxo-2-quinazolinylmethoxy]phenyl]methyl]-2,4-thiazolidinedione.

In one embodiment, the compounds of the formula I are administered in combination with an α-glucosidase inhibitor, such as, for example, miglitol or acarbose.

In one embodiment, the compounds of the formula I are administered in combination with an adenosine A1 agonist such as, for example, those described in EP 0912520 or PCT/EP06749.

In one embodiment, the compounds of the formula I are administered in combination with an active ingredient which acts on the ATP-dependent potassium channel of the beta cells, such as, for example, tolbutamide, glibenclamide, glipizide, glimepiride or repaglinide.

In one embodiment, the compounds of the formula I are administered in combination with more than one of the aforementioned compounds, e.g. in combination with a sulfonylurea and metformin, with a sulfonylurea and acarbose, repaglinide and metformin, insulin and a sulfonylurea, insulin and metformin, insulin and troglitazone, insulin and lovastatin, etc.

In a further embodiment, the compounds of the formula I are administered in combination with CART modulators (see "Cocaine-amphetamine-regulated transcript influences energy metabolism, anxiety and gastric emptying in mice" Asakawa, A, et al., M.: Hormone and Metabolic Research (2001), 33(9), 554-558), NPY antagonists, e.g. naphthalene-1-sulfonic acid {4-[((4-aminoquinazolin-2-ylamino)methyl] cyclohexylmethyl}amide, hydrochloride (CGP 71683A)), MC4 agonists (e.g. 1-amino-1,2,3,4-tetrahydronaphthalene-2-carboxylic acid [2-(3a-benzyl-2-methyl-3-oxo-2,3,3a,4,6,7-hexahydropyrazolo[4,3-c]pyridin-5-yl)-1-(4-chlorophenyl)-2-oxoethyl]amide; (WO 01/91752)), orexin antagonists (e.g. 1-(2-methylbenzoxazol-6-yl)-3-[1,5]naphthyridin-4-ylurea, hydrochloride (SB-334867-A)), H3 agonists (3-cyclohexyl-1-(4,4-dimethyl-1,4,6,7-tetrahydroimidazo[4,5-c]pyridin-5-yl)propan-1-one oxalic acid salt (WO 00/63208)); TNF agonists, CRF antagonists (e.g. [2-methyl-9-(2,4,6-trimethylphenyl)-9H-1,3,9-triazafluoren-4-yl]dipropylamine (WO 00/66585)), CRF BP antagonists (e.g. urocortin), urocortin agonists, β agonists (e.g. 1-(4-chloro-3-methanesulfonylmethylphenyl)-2-[2-(2,3-dimethyl-1H-indol-6-yloxy) ethyl-amino]ethanol hydrochloride (WO 01/83451)), CB1 (cannabinoid receptor 1) receptor antagonists (e.g. rimonabant or the active ingredients mentioned in WO 02/28346), MSH (melanocyte-stimulating hormone) agonists, CCK-A agonists (e.g. {2-[4-(4-chloro-2,5-dimethoxyphenyl)-5-(2-cyclohexylethyl)thiazol-2-ylcarbamoyl]-5,7-dimethylindol-1-yl}acetic acid trifluoroacetic acid salt (WO 99/15525)), serotonin reuptake inhibitors (e.g. dexfenfluramine), mixed serotoninergic and noradrenergic compounds (e.g. WO 00/71549), 5HT agonists e.g. 1-(3-ethylbenzofuran-7-yl)piperazine oxalic acid salt (WO 01/09111), bombesin agonists, galanin antagonists, growth hormone (e.g. human growth hormone), growth hormone-releasing compounds (6-benzyloxy-1-(2-diisopropylaminoethylcarbamoyl)-3,4-dihydro-1H-isoquinoline-2-carboxylic acid tertiary butyl ester (WO 01/85695)), TRH agonists (see, for example, EP 0 462 884), uncoupling protein 2 or 3 modulators, leptin agonists (see, for example, Lee, Daniel W.; Leinung, Matthew C.; Rozhavskaya-Arena, Marina; Grasso, Patricia. Leptin Agonists as a Potential Approach to the Treatment of Obesity. Drugs of the Future (2001), 26(9), 873-881), DA agonists (bromocriptine, Doprexin), lipase/amylase inhibitors (e.g. WO 00/40569), PPAR modulators (e.g. WO 00/78312), RXR modulators or TR-β agonists.

Other suitable combinations include the inventive compounds as defined in formula I together with another active ingredient such as leptin; (see, for example, "Perspectives in the Therapeutic Use of Leptin", Salvador, Javier; Gomez-Ambrosi, Javier; Fruhbeck, Gema, Expert Opinion on Pharmacotherapy (2001), 2(10), 1615-1622.), This article is also incorporated herein by reference.

In a further embodiment, the other active ingredient is selected from the group comprising rimonabant, dexamphetamine or amphetamine, fenfluramine or dexfenfluramine, sibutramine, orlistat, mazindol or phentermine.

In still yet another embodiment of the present invention, the compounds of the formula I are administered in combination with bulking agents, preferably insoluble bulking agents (see, for example, carob/Caromax® (Zunft H J; et al., Carob pulp preparation for treatment of hypercholesterolemia, Advances in Therapy (2001 September-October), 18(5), 230-6.) Caromax is a carob-containing product from Nutrinova, Nutrition Specialties & Food Ingredients GmbH, Industriepark Höchst, 65926 FrankfurtMain)). Combinations with Caromax® are also possible in one preparation or by separate administration of compounds of the formula I and Caromax®. Caromax® can in this connection also be administered in the form of food products such as, for example, in bakery products or muesli bars.

It is to be understood that various combinations of the compounds of the present invention may be formulated with one or more of the aforementioned compounds and optionally with one or more other pharmacologically active substances and these compositions as well are to be regarded as falling within the scope of the claims of the present application. Further to this end, the following structures are provided to more precisely and better define some of the aforementioned compounds not clearly delineated above that are useful in combination with those claimed herein.

JTT-705

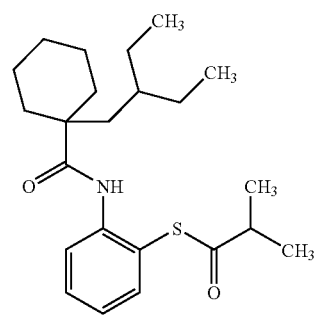

OPC-14117

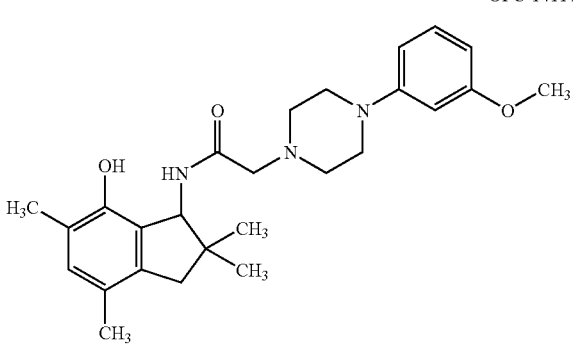

NO-1886

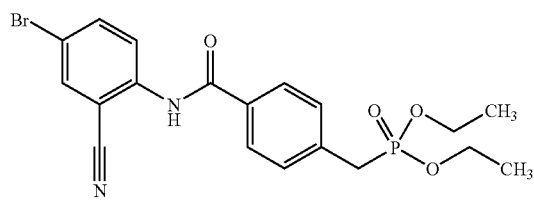

SB-204990

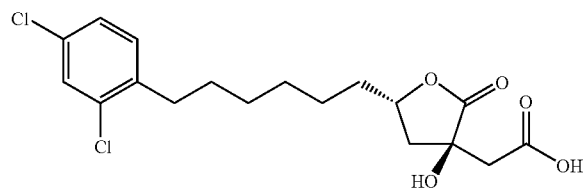

Cl-1027

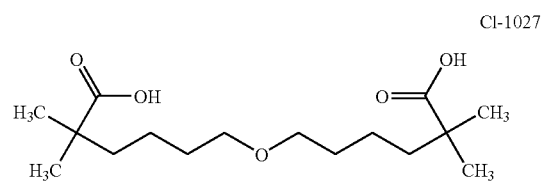

BMS-188494

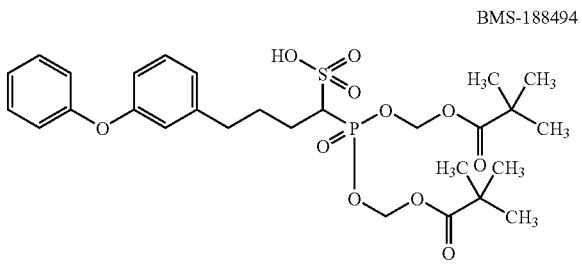

GI 262570

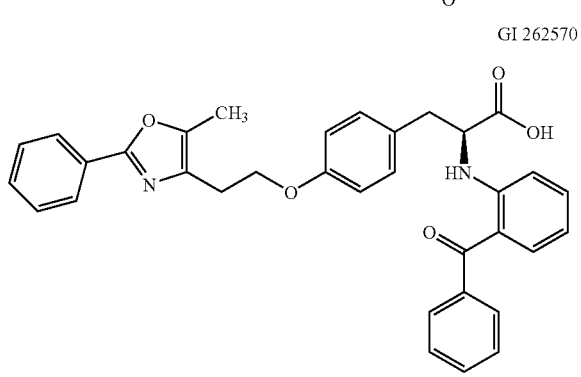

JTT-501

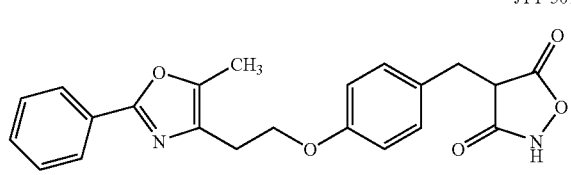

The compounds of formula I can be prepared by reacting suitable starting materials of the formula II in which X is a leaving group such as chlorine, bromine, iodine, sulfonyloxy, sulfonyl, sulfoxyl with a compound of the formula IV, where appropriate in the presence of suitable bases and in suitable solvent mixtures.

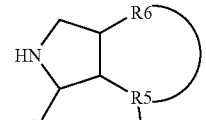

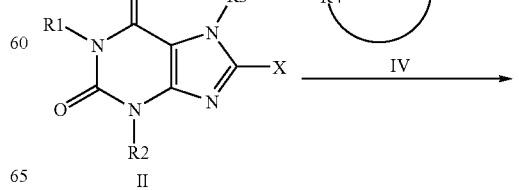

-continued

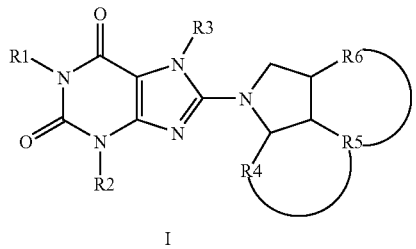

I

It may be expedient to use the residue of structure IV with the nitrogen function protected and then eliminate the protective group after reaction with II has taken place.

Such suitable protective groups and the methods for introduction and elimination are known (see: Theodora W. Greene and Peter G. M. Wuts, Protective Groups in Organic Synthesis, 3rd Edition, John Wiley & Sons, Inc., New York, 1999) which is also incorporated by reference herein. The halogen compounds of formula II can be obtained by known methods in the art such as, for example, by halogenation of the corresponding H or the hydroxy compound (formula II, X=H).

Suitable halogenating agents may be chlorine and bromine, N-bromosuccinimide, phosphorus pentachloride or phosphorus oxychloride.

Synthesis of compounds of the formula II is described in the literature, Houben Weyl E9b/2, pp. 331 et seq. and literature cited therein which is hereby incorporated by reference. They can be obtained starting from diaminopyridine derivatives or aminoimidazolecarboxamides by reaction with suitable reagents and be converted by targeted chemical modifications such as hydrolysis, alkylation, halogenation or acylation into the desired starting compounds of the formula II.

The substituent R-groups R1 to R3 can be prepared by methods as are known by those of skill in the art by alkylating appropriate known precursors, with the understanding that it is possible to vary the sequence accordingly. However, they can also be introduced by appropriate selection of suitable precursors for the preparation of the xanthine structure.

The synthesis of the bicyclic amines such as structure IV are also possible by methods disclosed in the literature or disclosed in the following examples The examples detailed below are provided to better describe and more specifically set forth the compounds, processes and methods of the present invention. It is to be recognized that they are for illustrative purposes only however, and should not be interpreted as limiting the spirit and scope of the invention as later recited by the claims that follow.

TABLE 1

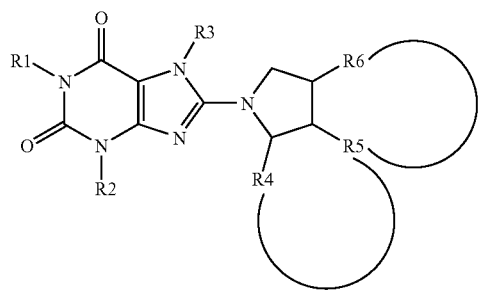

I

| Example | R1 | R2 | R3 | R4-R5 | R5-R6 | |
|---|---|---|---|---|---|---|
| 1 | —CH₂—CO—Phenyl | —CH₃ | —CH₂—CH=C—(CH₃)₂ | —CH₂—CH₂—NH— | R6 = H | |
| 1a | —CH₂—CO—Phenyl | —CH₃ | —CH₂—CH=C—(CH₃)₂ | —CH₂—CH₂—NH— | R6 = H | Diastereomer 1 |
| 1b | —CH₂—CO—Phenyl | —CH₃ | —CH₂—CH=C—(CH₃)₂ | —CH₂—CH₂—NH— | R6 = H | Diastereomer 2 |
| 2 | —CH₂—CH3 | —CH₃ | —CH₂—CH=C—(CH₃)₂ | —CH₂—CH₂—NH— | R6 = H | |
| 3b | —CH₂—CO—Phenyl | —CH₃ | —CH₂—CH=C—(CH₃)₂ | R4 = H | CH2—NH—CH2— | |

The compounds of the formula I exhibit superior beneficial effects on lipid and carbohydrate metabolism. In particular, they lower the blood glucose level and are suitable for the treatment of type 2 diabetes, insulin resistance, dyslipidemias and the metabolic syndrome/syndrome X. The compounds are also suitable for the prophylaxis and treatment of atherosclerotic manifestations. The compounds can be employed alone or in combination with other blood glucose-lowering active ingredients. The compounds act as dipeptidyl peptidase IV (DPP-IV) inhibitors and are also suitable for the treatment of disorders of wellbeing and other psychiatric indications such as, for example, depressions, anxiety states, anxiety neuroses, schizophrenia and for the treatment of disorders associated with the circadian rhythm, for weight reduction in mammals, for the treatment of immunological disorders, and for the treatment of drug abuse.

They are also suitable for the treatment of cancer, arthritis, osteoarthritis, osteoporosis, sleep disorders, sleep apnea, female and male sexual disorders, inflammations, acne, pigmentation of the skin, disorders of steroid metabolism, skin diseases, psoriasis, mycoses, neurodegenerative diseases, multiple sclerosis and Alzheimer's disease.

The activity of the compounds was assayed as follows:

Measurement of the DPP-IV Activity:

Material:

a) DPP-IV from porcine kidney (Sigma Chemical GmbH, Munich DE)

b) H-Ala-Pro-AFC (Bache Chemical Co., Weil am Rheine DE)

Assay Conditions:

c) DPP-IV (1 mU/ml, final concentration)

d) H-Ala-Pro-AFC (15 µM, final concentration)

in Tris/HCl (40 mM, pH 7.4), total volume 0.2 ml

The reaction was carried out at room temperature at different reaction times (typically 10 min) and stopped at the end of the reaction by adding 20 µl of $ZnCl_2$ (1 M). The H-Ala-Pro-AFC conversion was determined fluorimetrically by measuring the emission at 535 nm after excitation at 405 nm. When inhibitors were added, the added buffer volume was adapted so that a total volume of 200 µl was maintained for the assay mixture.

IC50 values for inhibitors were determined by varying the inhibitor concentrations with the stated substrate concentration of 15 µM. Ki and Km values were found by appropriate variation of substrate concentration and inhibitor concentration as described (Dixon, M. and Webb, E. C. (1979) Enzymes, third edition, pp. 47-206, Academic Press) which is herein incorporated by reference. The values for Km, IC50 and Ki were calculated using a commercially available software package (Leatherbarrow, R. J. (1992) GraFit Version 3.0, Erithacus Software Ltd. Staines, U.K.).

TABLE 2

Biological activity of exemplary embodiments:

| Exemplary embodiment No. | IC-50 | Remarks |
|---|---|---|
| 1 | 34 nM | |
| 1a | 160 nM | |
| 1b | 18 nM | |

It is clear from the table that the compounds of formula I inhibit the activity of DPP-IV (dipeptidyl peptidase IV) and superior agents for lowering the blood glucose level.

The preparation of some exemplary compounds is described in detail below, and other compounds of formula I were prepared similarity.

EXAMPLE 1

8-(cis-Hexahydro-pyrrolo[3,2-b]pyrrol-1-yl)-3-methyl-7-(3-methyl-but-2-enyl)-1-(2-oxo-2-phenylethyl)-3,7-dihydropurine-2,6-dione hydrochloride 400 mg of 8-bromo-3-methyl-7-(3-methyl-but-2-enyl)-1-(2-oxo-2-phenyl-ethyl)-3,7-dihydro-purine-2,6-dione were dissolved in 2 ml of N-methylpyrrolidone and, after addition of 130 mg of potassium carbonate and 200 mg of cis-octahydropyrrolo[3,2-b]pyrrole, stirred at 80° C. for 6 hours. The mixture was then diluted with 20 ml of water and extracted with ethyl acetate. The organic phase was dried over sodium sulfate and concentrated in a vacuum. The oily residue was purified by column chromatography (silica gel, mobile phase: methylene chloride: methanol=95:5). The resulting oily product was treated with 0.3 ml of a saturated hydrogen chloride solution in ethyl acetate, diluted with 5 ml of ethyl acetate, stirred and filtered off with suction as solid hydrochloride and dried in a vacuum.

Yield: 85 mg map.: 257° C. MS: M+1=463

This mixture of the two diastereoisomeric cis compounds was separated on a chiral column (Chiralpak AD 10×40 cm, manufactured by Merck; eluent: methanol +0.1% diethylamine;), and the following two products were obtained thereby:

EXAMPLE 1a 8-(cis-Hexahydro-pyrrolo[3,2-b]pyrrol-1-yl)-3-methyl-7-(3-methyl-but-2-enyl)-1-(2-oxo-2-phenylethyl)-3,7-dihydro-purine-2,6-dione Retention time: 9.3 min. (flow rate: 1 ml/min, MeOH +0.1% DEA)

m.p.: oil MS: M+1=463

EXAMPLE 1 b 8-(cis-Hexahydro-pyrrolo[3,2-b]pyrrol-1-yl)-3-methyl-7-(3-methyl-but-2-enyl)-1-(2-oxo-2-phenylethyl)-3,7-dihydro-purine-2,6-dione Retention time: 7.3 min. (flow rate: 1 ml/min, MeOH+ 0.1% DEA)

m.p.: oil MS: M+1=463

The cis-octahydro-pyrrolo[3,2-b]pyrrole employed as starting material was prepared by the following route via intermediates 1.1), 1.2) and 1.3):

1.1) Hexane-1,3,4,6-tetraol

4-Methylmorpholine 4-oxide (50%) in water) was slowly added to a mixture of hex-3-ene-1,6-diol (7.2 g), acetone (77 ml), water (150 ml), tert-butanol (77 ml), methanesulfonamide (5.9 g) and potassium osmate (228 mg). After 12 hours, the mixture was concentrated and purified by column chromatography on silica gel (mobile phase: ethyl acetate/methanol 3:1). The product with a molecular weight of 150.18 ($C_6H_{14}O_4$) was obtained in this way; MS (ESI): 151 (M+H+).

1.2) 1,3,4,6-Tetramethanesulfonyloxyhexane

Methanesulfonyl chloride (30.4 mL) was added to a solution of hexane-1,3,4,6-tetraol (8.3 g) in pyridine (150 mol) at −45° C. After a reaction time at ice-bath temperature of three hours, the mixture was poured into hydrochloric acid (4 N). The resulting precipitate was filtered off with suction. The product with a molecular weight of 462.54 (C10H22O12S4) was obtained in this way; MS (ESI): 463 (M+H+).

1.3) 1,4-Dibenzyl-octahydro-pyrrolo[3,2-b]pyrrole

A mixture of 1,3,4,6-tetramethanesulfonyloxyhexane (20.6 g), benzylamine (39.6 ml) and dioxane (550 ml) was boiled under reflux for three hours. The reaction solution was cooled, and triethylamine (60.5 ml) and acetyl chloride (25.9 ml) were added. After 40 minutes, the reaction mixture was concentrated and the residue was partitioned between hydrochloric acid (6 N) and ethyl acetate. The aqueous phase was made basic with sodium hydroxide solution (10 N) and extracted 4 times with ethyl acetate. The combined organic phases were dried over magnesium sulfate and concentrated. The product with the molecular weight of 292.43 (C20H24N2) was obtained in this way; MS (ESI): 293 (M+H+).

cis-Octahydro-pyrrolo[3,2-b]pyrrole

A solution of 1,4-dibenzyloctahydropyrrolo[3,2-b]pyrrole (2.4 g) in methanol (60 ml) was mixed with ammonium formate (2.1 g) and palladium hydroxide on carbon (20%, 0,12 g), and the mixture was boiled under reflux for 8 hours. After cooling, the reaction solution was filtered and concentrated. The crude product was immediately reacted further as in example 1).

The following were prepared in analogy to exemplary embodiment 1:

EXAMPLE 2

1-Ethyl-8-(cis-hexahydro-pyrrolo[3, 2-b]pyrrol-1-yl)-3-methyl-7-(3-methyl-but-2-enyl)-3,7-dihydropurine-2,6-dione m.p.: resin MS: M+1=373

EXAMPLE 3 a) tert-Butyl 5-[3-methyl-7-(3-methyl-but-2-enyl)-2, 6-dioxo-1-(2-oxo-2-phenyl-ethyl)-2,3,6,7-tetrahydro-1H-purin-8-yl]-cis-hexahydro-pyrrolo[3,4-c]pyrrole-2-carboxylate 52 mg of 8-bromo-3-methyl-7-(3-methyl-but-2-enyl)-1-(2-oxo-2-phenyl-ethyl)-3,7-dihydro-purine-2,6-dione were dissolved in 1 ml of DMF, and 56 mg of tert-butyl cis-hexahydropyrrolo[3,4-c]pyrrole-2-carboxylate and 36.5 mg of potassium carbonate were added. The mixture was stirred at 90° C. for 5 hours, cooled and evaporated in a vacuum. The oily residue was purified by column chromatography (silica gel: mobile phase: methylene chloride: methanol=98:2).

Yield: 55 mg m.p.: resin MS: M+1=563 b) 8-(cis-Hexahydro-pyrrolo[3,4-c]pyrrol-2-yl)-3-methyl-7-(3-methyl-but-2-enyl)-1-(2-oxo-2-phenyl-ethyl)-3,7-dihydro-purine-2,6-dione hydrochloride This compound was obtained by dissolving 50 mg of tert-butyl 5-[3-methyl-7-(3-methyl-but-2-enyl)-2,6-dioxo-1-(2-oxo-2-phenyl-ethyl)-2,3,6,7-tetrahydro-1H-purin-8-yl]-hexahydropyrrolo[3,4-c]pyrrole-2-carboxylate in 5 ml of ethyl acetate, treating the solution with excess hydrogen chloride solution in ethyl acetate, concentrating in a rotary evaporator and stirring with diisopropyl ether.

Yield: 45 mg m.p.: resin MS: M+1=463

What is claimed is:

1. A compound of formula I

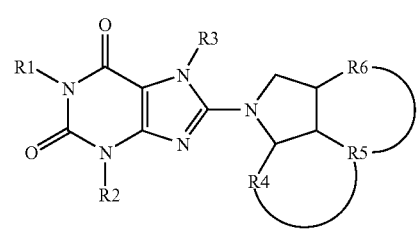

wherein:
R1, R2 and R3 independently of one another are selected from the group consisting of H, ($C_1$-$C_{10}$)-alkyl, ($C_3$-$C_{10}$)-cycloalkyl, ($C_2$-$C_{10}$)-alkenyl, ($C_2$-$C_{10}$)-alkynyl, ($C_6$-$C_{10}$)-aryl, and heterocycle, where the alkyl, cycloalkyl, alkenyl, alkynyl, aryl and heterocycle [R-]groups may be substituted one or more times by F, Cl, Br, I, CN, $NO_2$, SH, OH, ($C_1$-$C_6$)-alkyl, —$CF_3$, —$OCF_3$, —$SCF_3$, ($C_2$-$C_6$)-alkenyl, ($C_2$-$C_6$)-alkynyl, OR7, OP(O)(OR7)$_2$, NR7R8, NR7CONR7R8, COR7, OCOR7, OCOOR7, COOR7, CONR7R8, OCONR7R8, ($C_1$-$C_6$)-alkylene-OR7, ($C_1$-$C_6$)-alkylene-NR7R8, ($C_1$-$C_6$)-alkylene-NR7SO$_2$R7, ($C_1$-$C_6$)-alkylene-SR7, alkylene-S(O)R7, alkylene-S(O)$_2$R7, alkylene-S(O)$_2$NR7R8, ($C_1$-$C_6$)-alkylene-COR7, ($C_1$-$C_6$)-alkylene-COOR7, ($C_1$-$C_6$)-alkylene-CONR7R8, SR7, SOR7, SO$_2$R7, SO$_2$NR7R8, NR7SO$_2$R7, ($C_1$-$C_6$)-alkylene-($C_3$-$C_{10}$)-cycloalkyl, ($C_1$-$C_6$)-alkylene-($C_6$-$C_{10}$)-aryl, ($C_1$-$C_6$)-alkylene-heterocycle, ($C_3$-$C_{10}$)-cycloalkyl, ($C_6$-$C_{10}$)-aryl or heterocycle;
R7 and R8 independently of one another are selected from the group consisting of H, ($C_1$-$C_6$)-alkyl, —$CF_3$, ($C_3$-$C_{10}$)-cycloalkyl, ($C_6$-$C_{10}$)-aryl, heterocycle, ($C_1$-$C_6$)-alkylene-CONR9R10, CONR9R10, ($C_1$-$C_6$)-alkylene-COOR9, COOR9, COR9, ($C_1$-$C_6$)-alkylene-COR9, ($C_1$-$C_6$)-alkylene-OR9, ($C_1$-$C_6$)-alkylene-NR9R10, ($C_1$-$C_6$)-alkylene-SR9, ($C_1$-$C_6$)-alkylene-S(O)R9, ($C_1$-$C_6$)-alkylene-S(O)$_2$R9, S(O)R9, S(O)$_2$R9, ($C_1$-$C_4$)-alkylene-($C_6$-$C_{10}$)-aryl and ($C_1$-$C_4$)-alkylene-heterocycle;
R9 and R10 independently of one another are selected from the group consisting of H, ($C_1$-$C_6$)-alkyl, ($C_1$-$C_6$)-alkylene-($C_6$-$C_{10}$)-aryl, —($C_6$-$C_{10}$)-aryl, heterocycle, and ($C_1$-$C_6$)-alkylene-heterocycle;
R4 and R5 together form the group —$CH_2$—$CH_2$—NH—, where R6 is H, or
R5 and R6 together form the group —$CH_2$—NH—$CH_2$—, where R4 is H;
or a physiologically tolerated salt thereof.

2. The compound of the formula I as recited in claim 1, wherein:
R1, R2 and R3 independently of one another are selected from the group consisting of H, ($C_1$-$C_{10}$)-alkyl, ($C_3$-$C_{10}$)-cycloalkyl, ($C_2$-$C_{10}$)-alkenyl, ($C_2$-$C_{10}$)-alkynyl, ($C_6$-$C_{10}$)-aryl, and heterocyclyl, where the alkyl, cycloalkyl, alkenyl, alkynyl, aryl and heterocyclyl [R-]groups may be substituted one or more times by F, Cl, Br, I, CN, $NO_2$, SH, OH, ($C_1$-$C_6$)-alkyl, —$CF_3$, —$OCF_3$, —$SCF_3$, ($C_2$-$C_6$)-alkenyl, ($C_2$-$C_6$)-alkynyl, OR7, OP(O)(OR7)$_2$, NR7R8, NR7CONR7R8, COR7, OCOR7, OCOOR7, COOR7, CONR7R8, OCONR7R8, ($C_1$-$C_6$)-alkylene-OR7, ($C_1$-$C_6$)-alkylene-NR7R8, ($C_1$-$C_6$)-alkylene-NR7SO$_2$R7, ($C_1$-$C_6$)-alkylene-SR7, alkylene-S(O)R7, alkylene-S(O)$_2$R7, alkylene-S(O)$_2$NR7R8, ($C_1$-$C_6$)-alkylene-COR7, ($C_1$-$C_6$)-alkylene-COOR7, ($C_1$-$C_6$)-alkylene-CONR7R8, SR7, SORT, SO$_2$R7, SO$_2$NR7R8, NR7SO$_2$R7, ($C_1$-$C_6$)-alkylene-($C_3$-$C_{10}$)-cycloalkyl, ($C_1$-$C_6$)-alkylene-($C_6$-$C_{10}$)-aryl, ($C_1$-$C_6$)-alkylene-heterocycle, ($C_3$-$C_{10}$)-cycloalkyl, ($C_6$-$C_{10}$)-aryl or heterocyclyl;

R7 and R8 independently of one another are selected from the group consisting of H, ($C_1$-$C_6$)-alkyl, —CF$_3$, ($C_3$-$C_{10}$)-cycloalkyl, ($C_6$-$C_{10}$)-aryl, heterocycle, ($C_1$-$C_6$)-alkylene-CONR9R10, CONR9R10, ($C_1$-$C_6$)-alkylene-COOR9, COOR9, COR9, ($C_1$-$C_6$)-alkylene-COR9, ($C_1$-$C_6$)-alkylene-OR9, ($C_1$-$C_6$)-alkylene-NR9R10, ($C_1$-$C_6$)-alkylene-SR9, ($C_1$-$C_6$)-alkylene-S(O)R9, ($C_1$-$C_6$)-alkylene-S(O)$_2$R9, S(O)R9, S(O)$_2$R9, ($C_1$-$C_4$)-alkylene-($C_6$-$C_{10}$)-aryl and ($C_1$-$C_4$)-alkylene-heterocycle;

R9 and R10 independently of one another are selected from the group consisting of H, ($C_1$-$C_6$)-alkyl, ($C_1$-$C_6$)-alkylene-($C_6$-$C_{10}$)-aryl, —($C_6$-$C_{10}$)-aryl, heterocyclyl, and ($C_1$-$C_6$)-alkylene-heterocyclyl;

R4 and R5 together form the group —CH$_2$—CH$_2$—NH—; and

R6 is H;

or a physiologically tolerated salt thereof.

3. The compound of formula I as recited in claim 2, wherein:

R1 is ($C_1$-$C_{10}$)-alkyl, where the alkyl radical may be substituted by COR7;

R2 is ($C_1$-$C_{10}$)-alkyl;

R3 is ($C_1$-$C_{10}$)-alkyl, ($C_2$-$C_{10}$)-alkenyl;

R7 is ($C_6$-$C_{10}$)-aryl;

R4 and R5 together form the group —CH$_2$—CH$_2$—NH—; and

R6 is H;

or a physiologically tolerated salt thereof.

4. A pharmaceutical composition comprising a compound selected from the group consisting of those as recited in claim 1 in combination with at least one additional agent consisting of one or more excipients, bulking agents, fillers stabilizers, tableting agents, solvents, solubilizers and mixtures thereof.

5. A pharmaceutical composition comprising a compound selected from the group consisting of those as recited in claim 3 in combination with at least one additional agent consisting of one or more excipients, bulking agents, fillers stabilizers, tableting agents, solvents, solubilizers and mixtures thereof.

6. A method for the treatment of elevated blood glucose levels and the diseases associated therewith consisting of the administration of a pharmaceutical composition comprising one or more compounds selected from the group consisting of a compound of formula I:

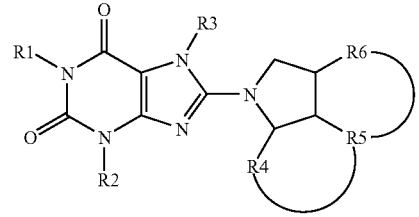

wherein:

R1, R2 and R3 independently of one another are selected from the group consisting of H, ($C_1$-$C_{10}$)-alkyl, ($C_3$-$C_{10}$)-cycloalkyl, ($C_2$-$C_{10}$)-alkenyl, ($C_2$-$C_{10}$)-alkynyl, ($C_6$-$C_{10}$)-aryl, heterocycle, where the alkyl, cycloalkyl, alkenyl, alkynyl, aryl and heterocycle R-groups may be substituted one or more times by F, Cl, Br, I, CN, NO$_2$, SH, OH, ($C_1$-$C_6$)-alkyl, —CF$_3$, —OCF$_3$, —SCF$_3$, ($C_2$-$C_6$)-alkenyl, ($C_2$-$C_6$)-alkynyl, OR7, OP(O)(OR7)$_2$, NR7R8, NR7CONR7R8, COR7, OCOR7, OCOOR7, COOR7, CONR7R8, OCONR7R8, ($C_1$-$C_6$)-alkylene-OR7, ($C_1$-$C_6$)-alkylene-NR7R8, ($C_1$-$C_6$)-alkylene-NR7SO$_2$R7, ($C_1$-$C_6$)-alkylene-SR7, alkylene-S(O)R7, alkylene-S(O)$_2$R7, alkylene-S(O)$_2$NR7R8, ($C_1$-$C_6$)-alkylene-COR7, ($C_1$-$C_6$)-alkylene-COOR7, ($C_1$-$C_6$)-alkylene-CONR7R8, SR7, SORT, SO$_2$R7, SO$_2$NR7R8, NR7SO$_2$R7, ($C_1$-$C_6$)-alkylene-($C_3$-$C_{10}$)-cycloalkyl, ($C_1$-$C_6$)-alkylene-($C_6$-$C_{10}$)-aryl, ($C_1$-$C_6$)-alkylene-heterocycle, ($C_3$-$C_{10}$)-cycloalkyl, ($C_6$-$C_{10}$)-aryl or heterocycle;

R7 and R8 independently of one another are selected from the group consisting of H, ($C_1$-$C_6$)-alkyl, —CF$_3$, ($C_3$-$C_{10}$)-cycloalkyl, ($C_6$-$C_{10}$)-aryl, heterocycle, $C_1$-$C_6$)-alkylene-CONR9R10, CONR9R10, ($C_1$-$C_6$)-alkylene-COOR9, COOR9, COR9, ($C_1$-$C_6$)-alkylene-COR9, ($C_1$-$C_6$)-alkylene-OR9, ($C_1$-$C_6$)-alkylene-NR9R10, ($C_1$-$C_6$)-alkylene-SR9, ($C_1$-$C_6$)-alkylene-S(O)R9, ($C_1$-$C_6$)-alkylene-S(O)$_2$R9, S(O)R9, S(O)$_2$R9, ($C_1$-$C_4$)-alkylene-($C_6$-$C_{10}$)-aryl or ($C_1$-$C_4$)-alkylene-heterocycle;

R9 and R10 independently of one another are selected from the group consisting of H, ($C_1$-$C_6$)-alkyl, ($C_1$-$C_6$)-alkylene-($C_6$-$C_{10}$)-aryl, —($C_6$-$C_{10}$)-aryl, heterocycle, ($C_1$-$C_6$)-alkylene-heterocycle;

R4 and R5 together form the group —CH$_2$—CH$_2$—NH—, where R6 is H, or

R5 and R6 together form the group —CH$_2$—NH—CH$_2$—, where R4 is H;

or a physiologically tolerated salt thereof in a pharmaceutically acceptable carrier.

7. A process for the preparation of a pharmaceutical composition consisting of one or more of the compounds as recited in claim 3, wherein the compound as defined by formula I is mixed with a pharmaceutically suitable carrier comprising one or more excipients, bulking agents, fillers, stabilizers, tableting agents, solvents, solubilizers and mixtures thereof which is formulated suitable for administration to a patient in need thereof.

* * * * *

UNITED STATES PATENT AND TRADEMARK OFFICE
CERTIFICATE OF CORRECTION

| | | |
|---|---|---|
| PATENT NO. | : 7,838,528 B2 | Page 1 of 2 |
| APPLICATION NO. | : 11/623770 | |
| DATED | : November 23, 2010 | |
| INVENTOR(S) | : Karl Schoenafinger et al. | |

It is certified that error appears in the above-identified patent and that said Letters Patent is hereby corrected as shown below:

On the Title Page, Item (56) under "Other Publications", line 1, after "of" insert -- a --.

On the Title Page, Item (56) under "Other Publications", line 6, delete "meilitus ," and insert -- mellitus, --, therefor.

In column 1, line 12, delete "it's'" and insert -- it's --, therefor.

In column 1, line 37, delete "animals" and insert -- animals. --, therefor.

In column 2, line 8, delete "reference" and insert -- reference. --, therefor.

In column 4, line 67, delete "S—$(CH_2)$n" and insert -- S—$(CH_2)_n$ --, therefor.

In column 8, line 17, delete "S—$(CH_2)$n" and insert -- S—$(CH_2)_n$ --, therefor.

In column 8, line 18, delete "S—$(CH_2)$n" and insert -- S—$(CH_2)_n$ --, therefor.

In column 8, line 18, delete "SO—$(CH_2)$n" and insert -- SO—$(CH_2)_n$ --, therefor.

In column 8, line 20, delete "NH$(CH_2)$n" and insert -- NH$(CH_2)_n$ --, therefor.

In column 8, line 21, delete "$SO_2$-N($(CH_2)$n" and insert -- $SO_2$-NH$(CH_2)_n$ --, therefor.

In column 8, line 66-67, delete "benzisoxazolyi," and insert -- benzisoxazolyl, --, therefor.

In column 8, line 67, delete "benzimidazalinyl," and insert -- benzimidazolinyl, --, therefor.

In column 9, line 15, delete "pyroazolidinyl," and insert -- pyrazolidinyl, --, therefor.

Signed and Sealed this
Thirteenth Day of December, 2011

David J. Kappos
*Director of the United States Patent and Trademark Office*

CERTIFICATE OF CORRECTION (continued)
U.S. Pat. No. 7,838,528 B2

In column 9, line 19, delete "6H-1,2,5-thiadazinyl," and insert -- 6H-1,2,5-thiadiazinyl, --, therefor.

In column 9, line 20, delete "1,2,4-thiadiazolyi," and insert -- 1,2,4-thiadiazolyl, --, therefor.

In column 12, line 50, delete "mazindol" and insert -- Mazindol --, therefor.

In column 13, line 67, delete "al.)," and insert -- al.). --, therefor.

In column 13, line 10, delete "al.)," and insert -- al.). --, therefor.

In column 15, line 2, delete "FrankfurtMain))." and insert -- Frankfurt/Main)). --, therefor.

In column 18, line 23, delete "examples" and insert -- examples. --, therefor.

In column 23, line 7, in claim 2, delete "SORT," and insert -- SOR7, --, therefor.

In column 24, line 15, in claim 6, delete "($C_1$-$C_{10}$-alkyl," and insert -- "($C_1$-$C_{10}$)-alkyl, --, therefor.

In column 24, line 28, in claim 6, delete "SORT," and insert -- SOR7, --, therefor.

In column 24, line 36, in claim 6, delete "$C_1$-$C_6$)-" and insert -- ($C_1$-$C_6$)- --, therefor.